US010925961B2

(12) United States Patent
Weiner et al.

(10) Patent No.: US 10,925,961 B2
(45) Date of Patent: Feb. 23, 2021

(54) VACCINES WITH CD40 LIGAND AS AN ADJUVANT

(71) Applicants: The Trustees of the University of Pennsylvania, Philadelphia, PA (US); INOVIO PHARMACEUTICALS, INC., Plymouth Meeting, PA (US)

(72) Inventors: David Weiner, Merion, PA (US); Matthew Morrow, Bala Cynwyd, PA (US); Megan Wise, Raleigh, NC (US)

(73) Assignees: The Trustees of the University of Pennsylvania, Philadelphia, PA (US); INOVIO PHARMACEUTICALS. INC., Plymouth Meeting, PA (US)

( * ) Notice: Subject to any disclaimer, the term of this patent is extended or adjusted under 35 U.S.C. 154(b) by 316 days.

(21) Appl. No.: 15/559,432

(22) PCT Filed: Mar. 18, 2016

(86) PCT No.: PCT/US2016/023126
§ 371 (c)(1),
(2) Date: Sep. 19, 2017

(87) PCT Pub. No.: WO2016/153995
PCT Pub. Date: Sep. 29, 2016

(65) Prior Publication Data
US 2018/0085451 A1    Mar. 29, 2018

Related U.S. Application Data

(60) Provisional application No. 62/136,283, filed on Mar. 20, 2015, provisional application No. 62/303,984, filed on Mar. 4, 2016.

(51) Int. Cl.
| A61K 39/39 | (2006.01) |
| A61K 39/12 | (2006.01) |
| A61P 31/20 | (2006.01) |
| A61P 31/16 | (2006.01) |
| A61P 35/00 | (2006.01) |
| A61K 39/00 | (2006.01) |
| C07K 14/705 | (2006.01) |
| A61K 39/145 | (2006.01) |
| A61K 39/21 | (2006.01) |
| A61K 41/00 | (2020.01) |

(52) U.S. Cl.
CPC .......... *A61K 39/39* (2013.01); *A61K 39/0011* (2013.01); *A61K 39/12* (2013.01); *A61K 39/145* (2013.01); *A61K 39/21* (2013.01); *A61P 31/16* (2018.01); *A61P 31/20* (2018.01); *A61P 35/00* (2018.01); *C07K 14/70575* (2013.01); *C07K 14/70578* (2013.01); *A61K 2039/53* (2013.01); *A61K 2039/55516* (2013.01); *A61K 2039/585* (2013.01); *C12N 2710/20034* (2013.01); *C12N 2740/16134* (2013.01); *C12N 2760/16134* (2013.01); *Y02A 50/30* (2018.01)

(58) Field of Classification Search
CPC ....... A61K 39/39; C07K 14/005; C12N 11/08
USPC ...................................................... 424/186.1
See application file for complete search history.

(56) References Cited

U.S. PATENT DOCUMENTS

| 2012/0076820 A1 | 3/2012 | Amara et al. |
| 2013/0052222 A1 | 2/2013 | Weiner et al. |
| 2013/0302367 A1 | 11/2013 | Shida et al. |
| 2014/0080208 A1 | 3/2014 | Deisseroth et al. |
| 2014/0107189 A1 | 4/2014 | Chakraborty et al. |

FOREIGN PATENT DOCUMENTS

| CN | 102154306 A | 8/2011 |
| WO | 2001056602 A2 | 8/2001 |
| WO | 2004044175 A2 | 5/2004 |
| WO | 2014145355 A1 | 9/2014 |
| WO | 2016137162 A1 | 9/2016 |
| WO | 2016141068 A1 | 9/2016 |

OTHER PUBLICATIONS

Chinchilla et al. "Enhanced Immunity to Plasmodium falciparum Circumsporozoite Protein (PfCSP) by Using *Salmonella enterica* Serovar Typhi Expressing PfCSP and a PfCSP-Encoding DNA Vaccine in a Heterologous Prime-Boost Strategy" Infect Immun., 2007, 75:3769-3779.
Database WPI Week 201164 Thomson Scientific, London, GB; AN 2011-L59994 XP002785819, & CN 102 154 306 A (Nat Res Cent Veterinary Biologicals Eng), Aug. 17, 2011.

*Primary Examiner* — Bao Q Li
(74) *Attorney, Agent, or Firm* — Riverside Law LLP

(57) ABSTRACT

Disclosed herein is a vaccine comprising an antigen and CD40L. Also disclosed herein are methods for increasing an immune response in a subject. The methods may comprise administering the vaccine to the subject in need thereof.

18 Claims, 29 Drawing Sheets
Specification includes a Sequence Listing.

FIGURE 1A
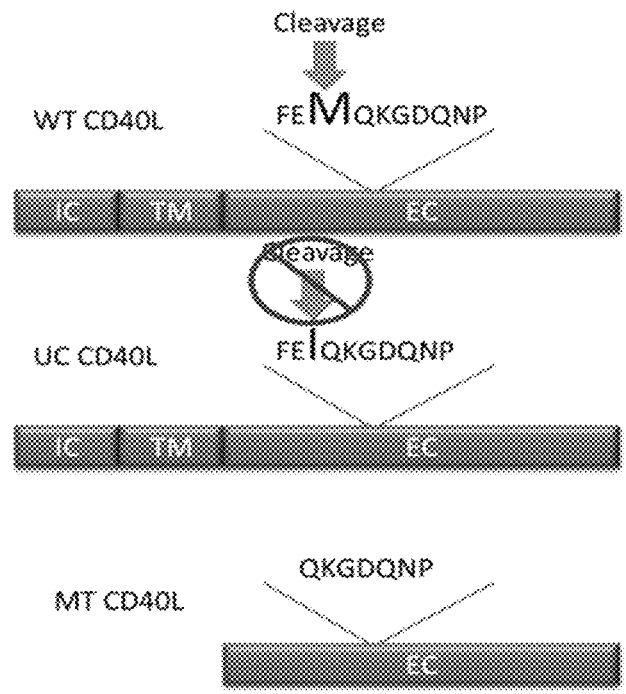
FIGURE 1B
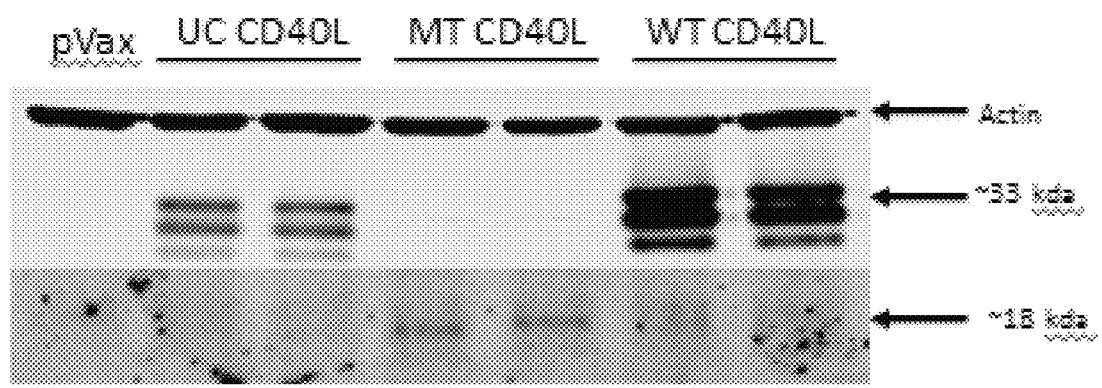
FIGURE 1

FIGURE 2A
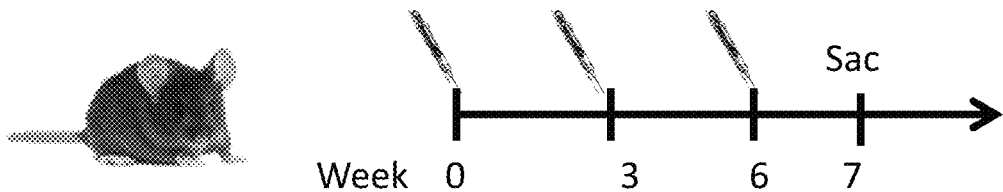
FIGURE 2B
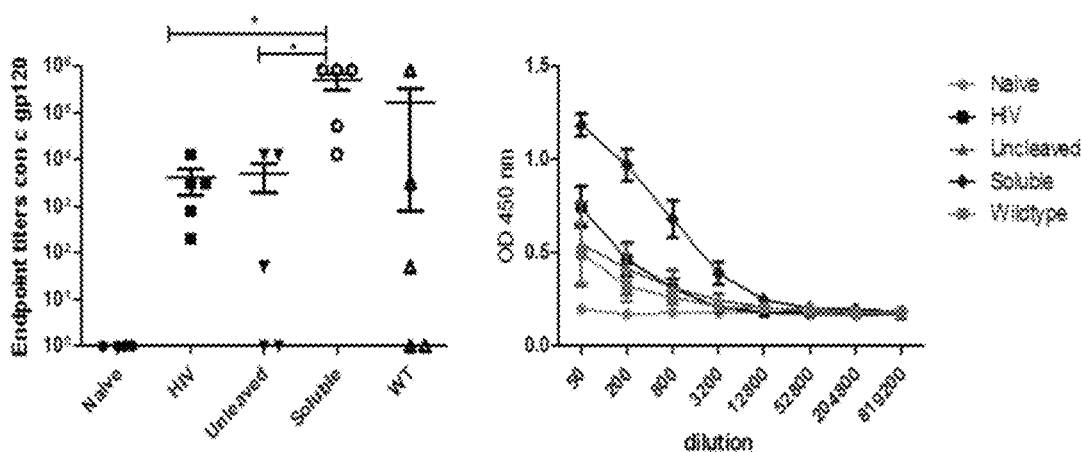
FIGURE 2

FIGURE 3A
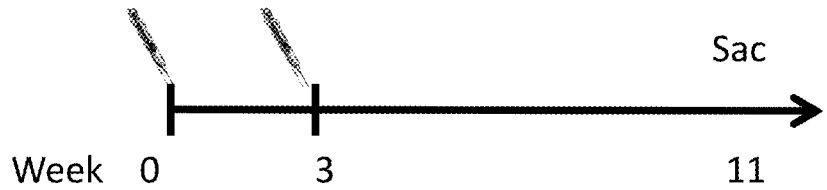
FIGURE 3B
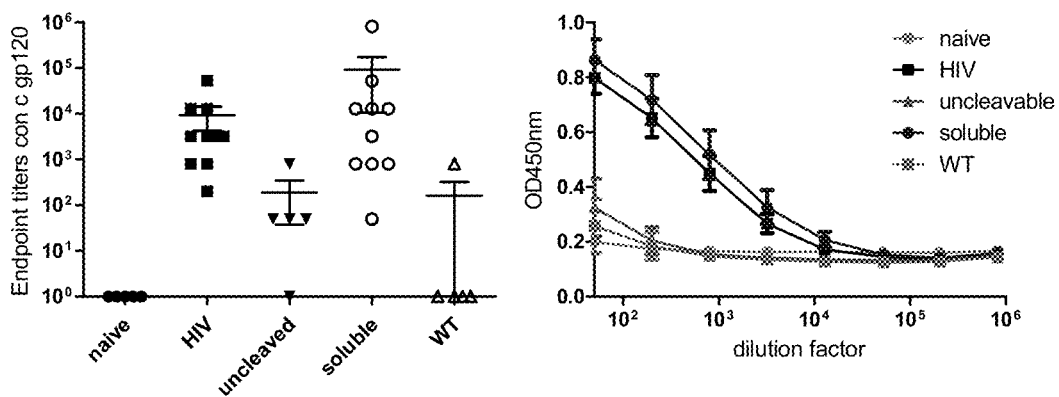
FIGURE 3C
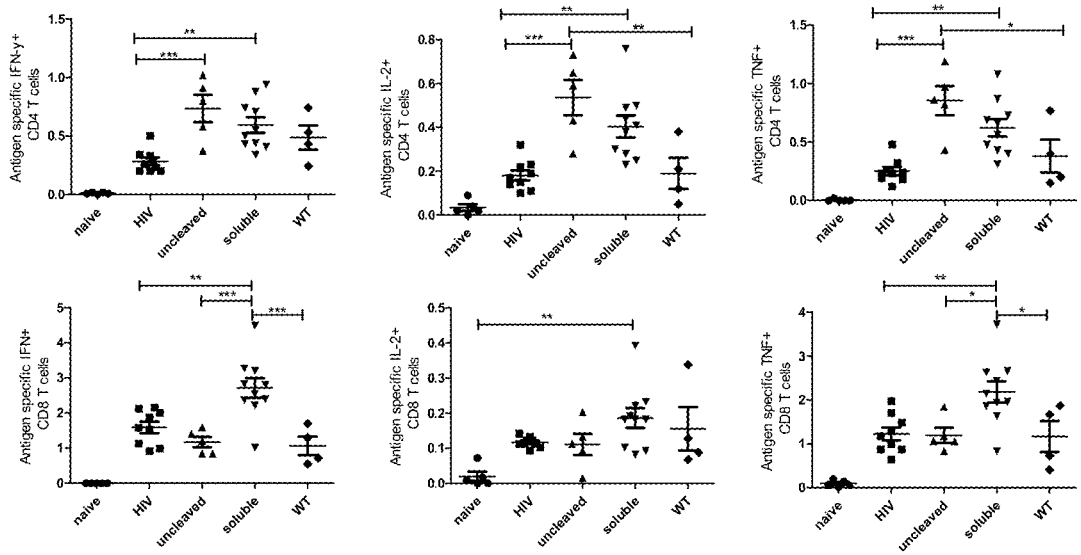
FIGURE 3

FIGURE 4A
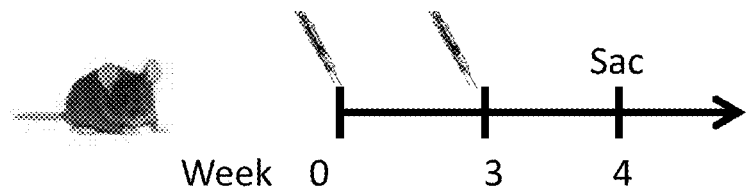
FIGURE 4B
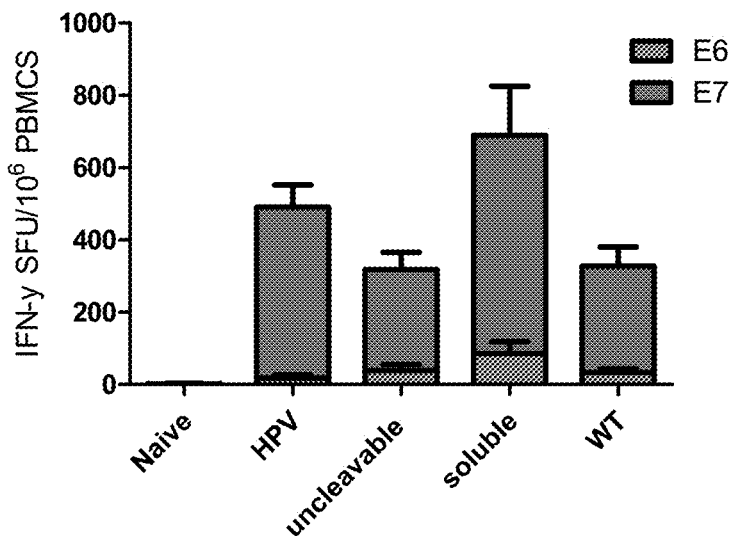
FIGURE 4C
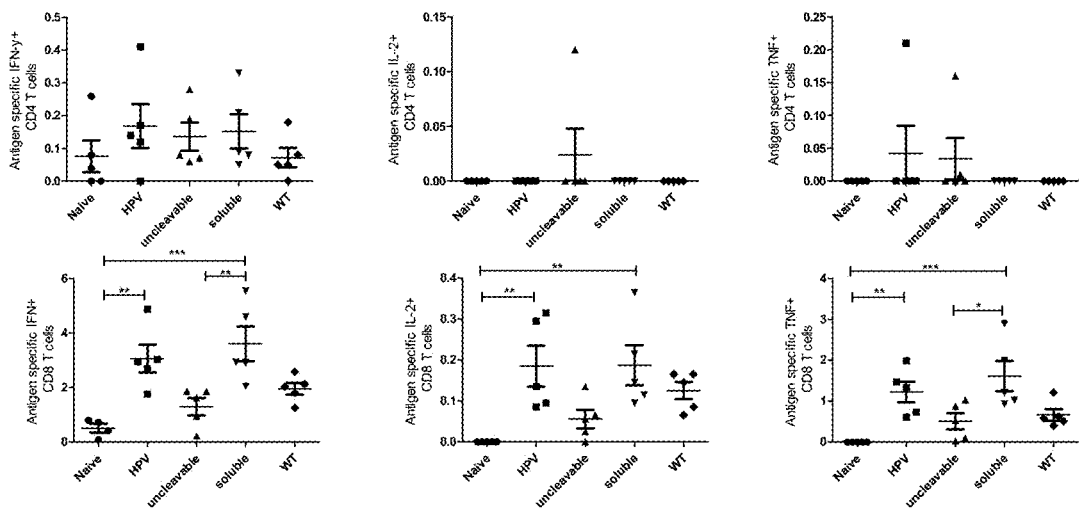
FIGURE 4

FIGURE 4D
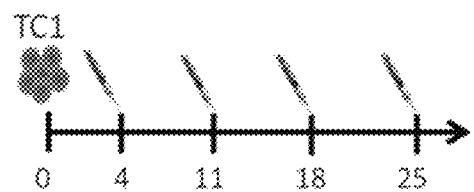
FIGURE 4E
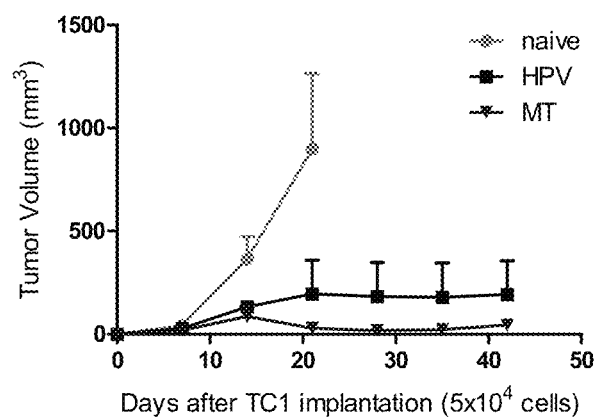
FIGURE 4 (cont.)

FIGURE 5A
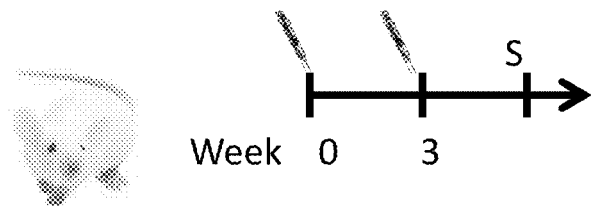
FIGURE 5B
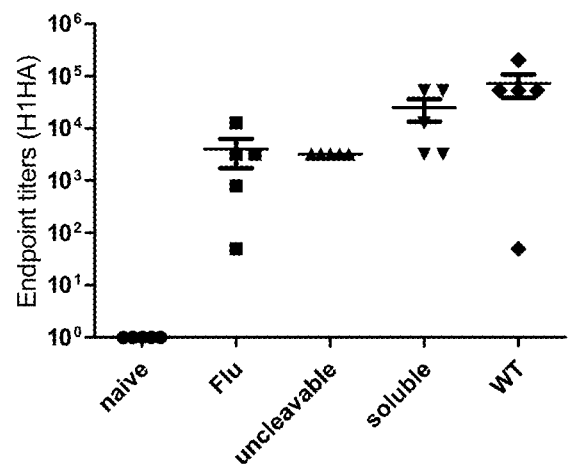
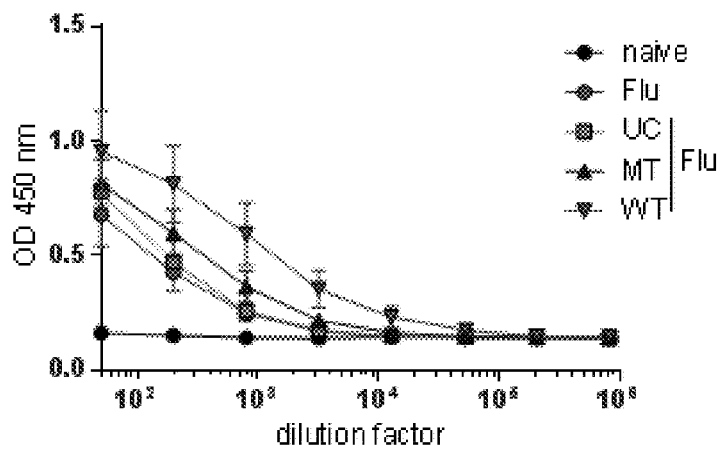
FIGURE 5

FIGURE 6A
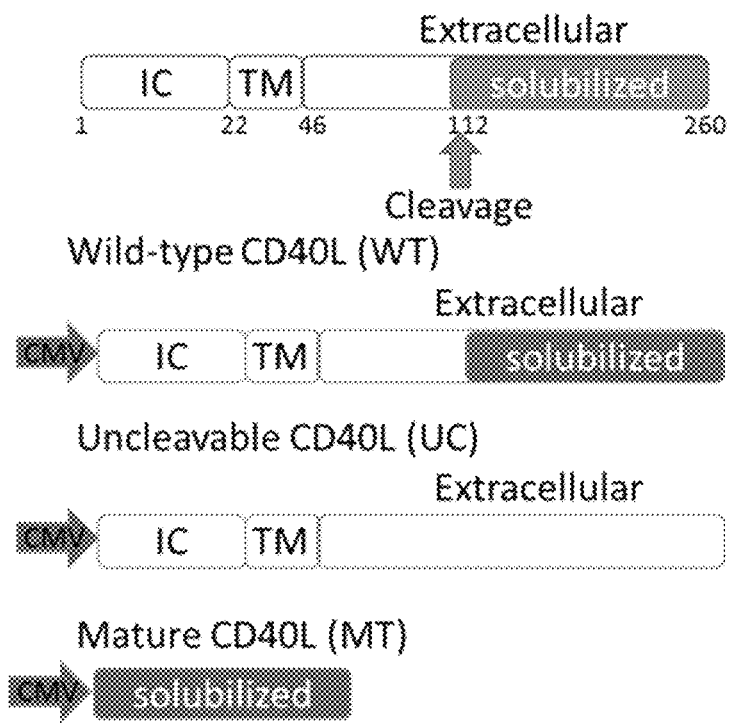
FIGURE 6B
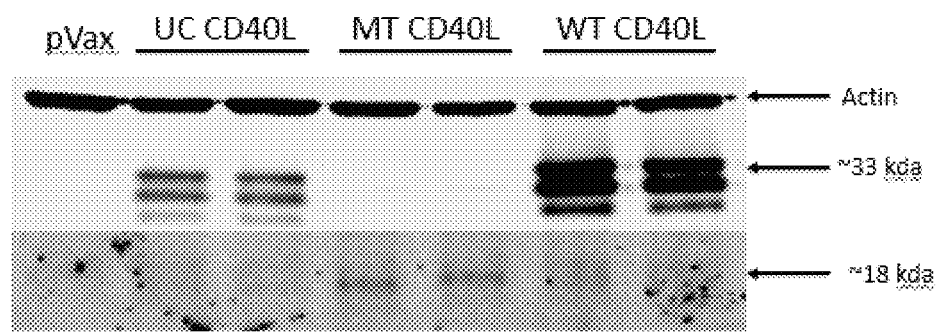
FIGURE 6

FIGURE 7A
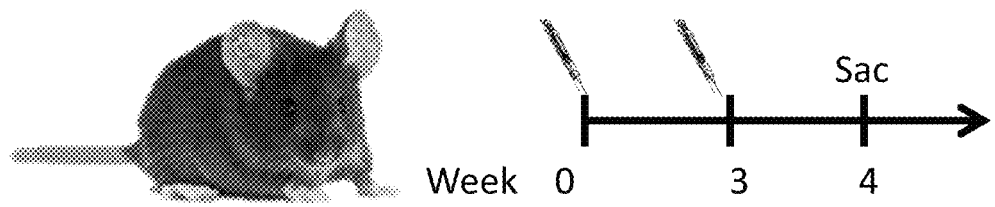
FIGURE 7B
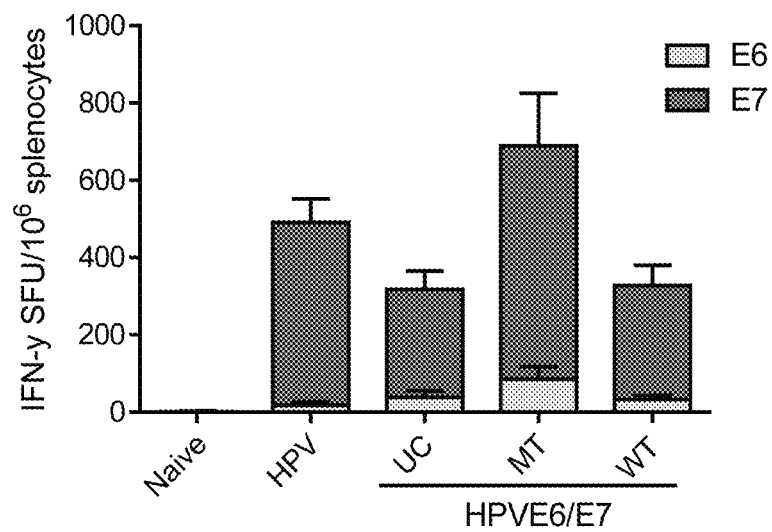
FIGURE 7

FIGURE 7C
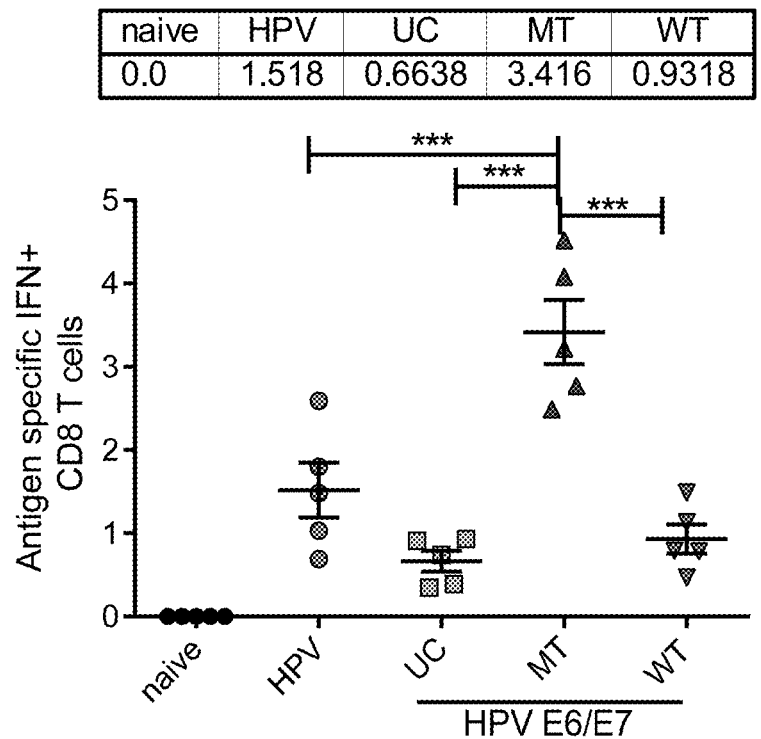
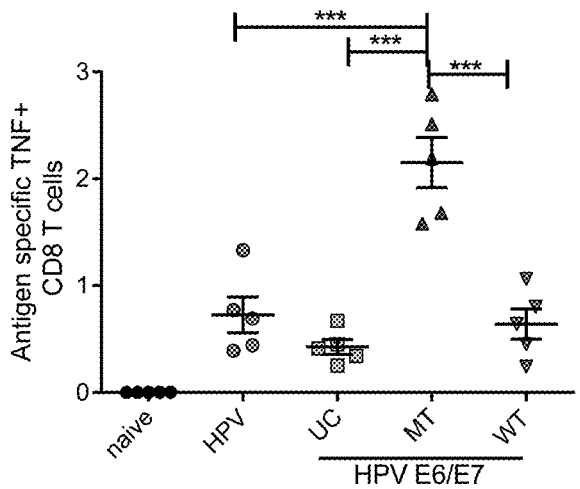
FIGURE 7 (cont.)

FIGURE 7D
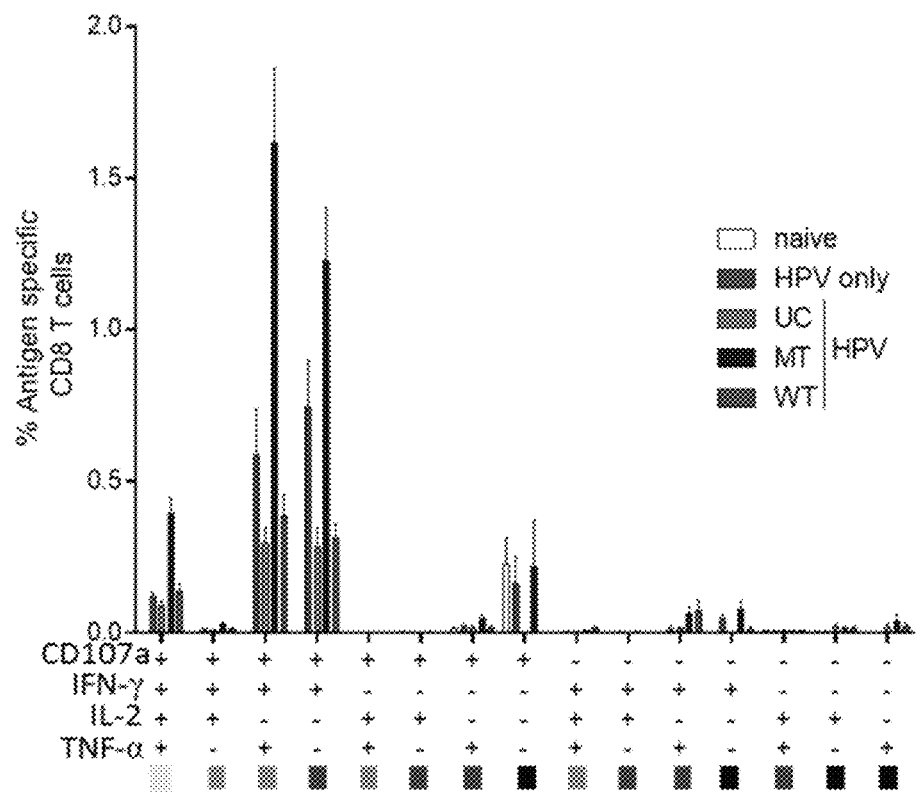
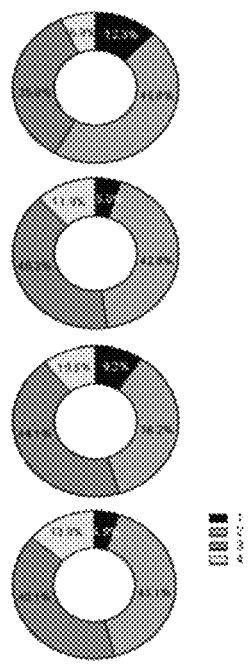
FIGURE 7 (cont.)

FIGURE 8A
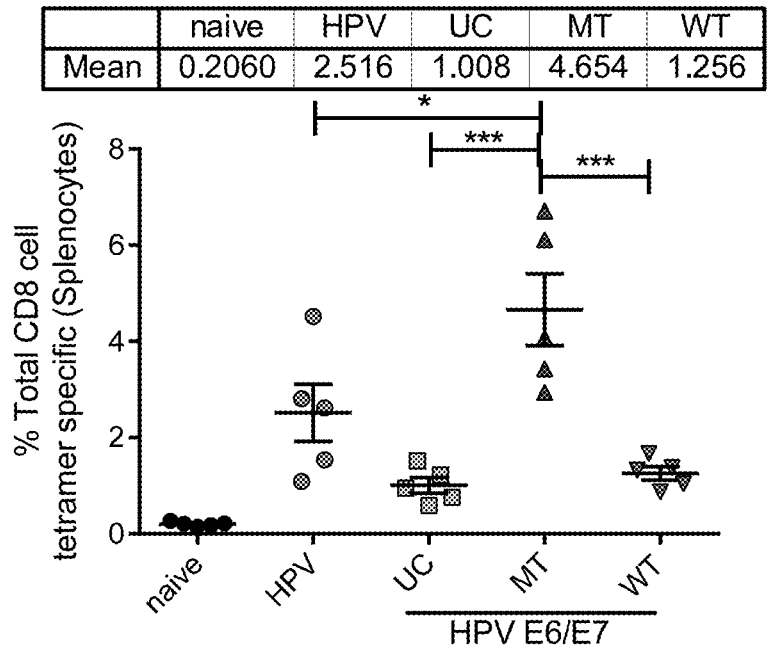
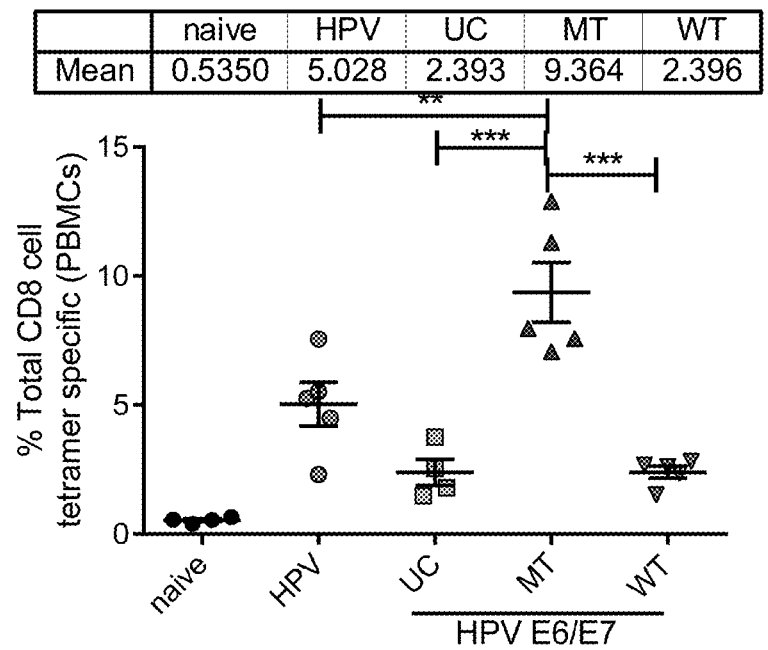
FIGURE 8

| Days | Means | | | |
|---|---|---|---|---|
| | HPV | UC | MT | WT |
| 8 | 0.304 | 0.994 | 0.562 | 1.688 |
| 11 | 2.852 | 3.86 | 16.92 | 3.892 |
| 14 | 2.827 | 1.906 | 8.903334 | 1.974445 |
| 21 | 1.964 | 0.941 | 3.444667 | 0.844445 |
| 25 | 1.598 | 0.646 | 2.156 | 0.694 |
| 28 | 4.039 | 2.382 | 4.887143 | 2.482222 |
| 35 | 2.99 | 2.264 | 5.662 | 1.864 |
| 42 | 2.1075 | 1.672 | 4.742 | 1.246 |

FIGURE 8C
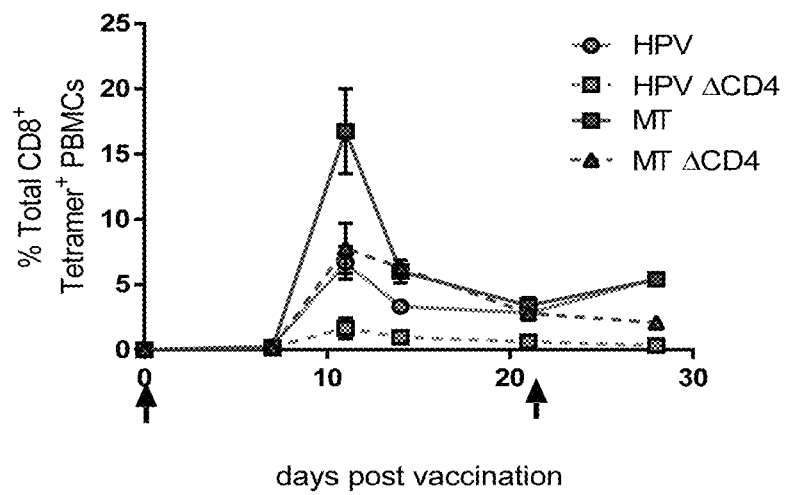
| Days | HPV only | HPV only delta CD4 | MT | MT delta CD4 |
|---|---|---|---|---|
| 0 | 0 | 0 | 0 | 0 |
| 7 | 0.2525 | 0.198 | 0.13 | 0.152 |
| 11 | 6.675 | 1.646 | 16.7525 | 7.788 |
| 14 | 3.315 | 0.97 | 6.0175 | 6.308 |
| 21 | 2.83 | 0.622 | 3.375 | 2.794 |
| 28 | 5.4175 | 0.3476 | 5.4 | 2.084 |
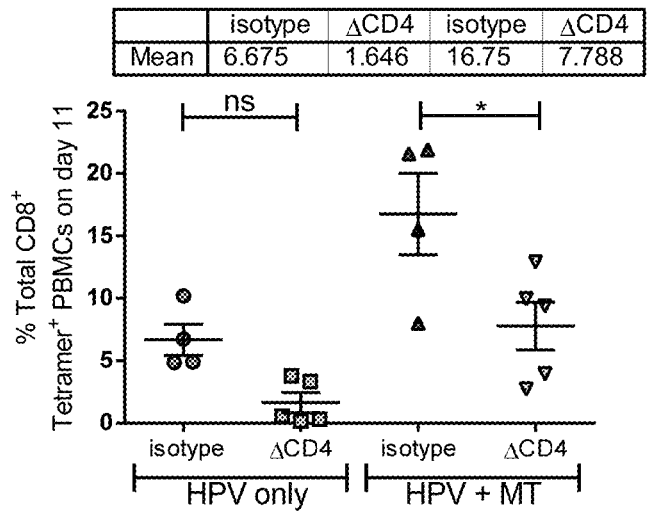
|  | isotype | ΔCD4 | isotype | ΔCD4 |
|---|---|---|---|---|
| Mean | 6.675 | 1.646 | 16.75 | 7.788 |
FIGURE 8 (cont.)

FIGURE 8C (cont.)
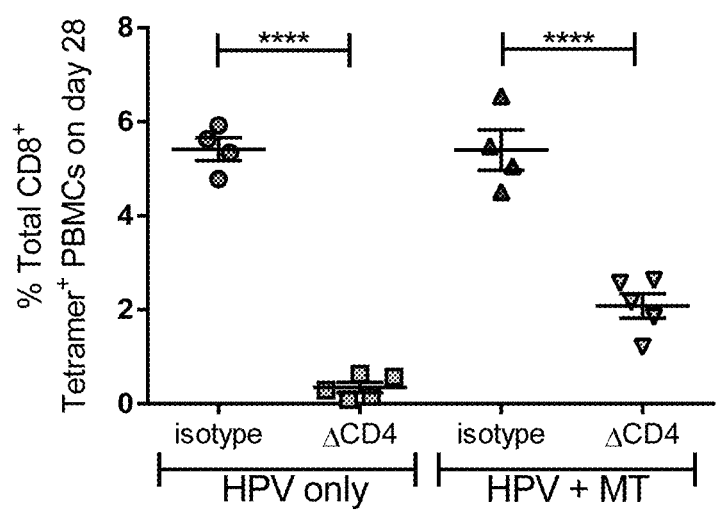
FIGURE 8D
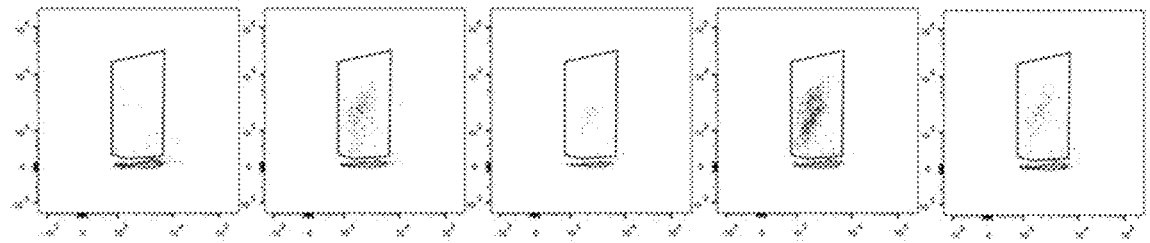
FIGURE 8 (cont.)

FIGURE 9A
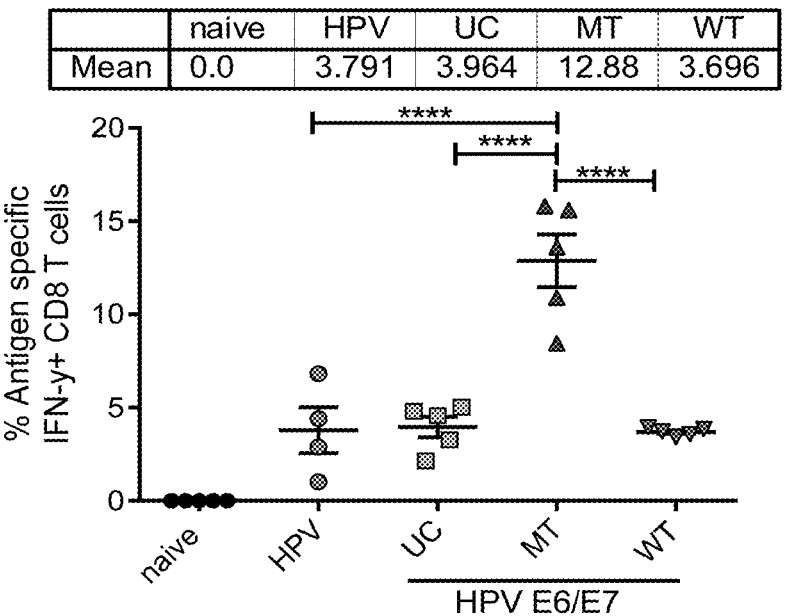
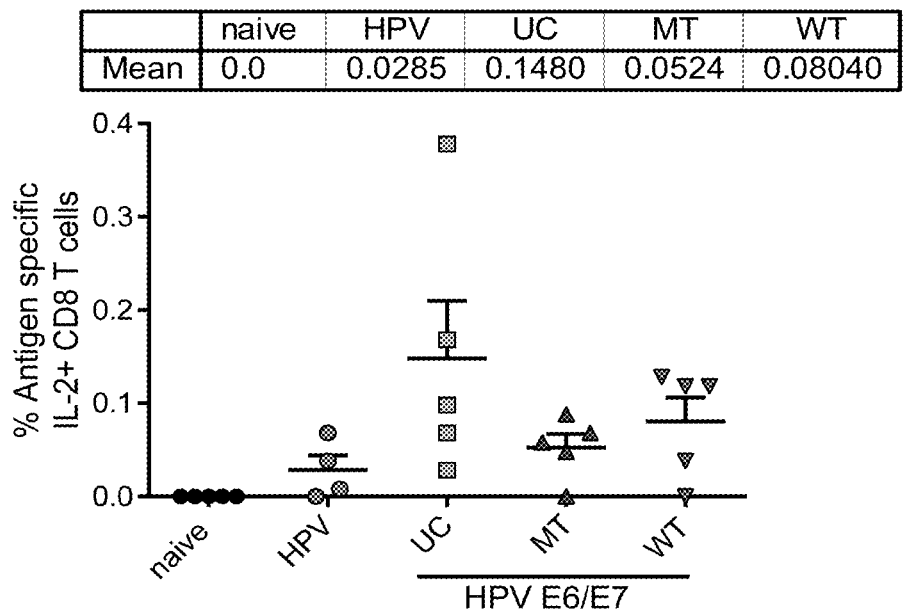
FIGURE 9

FIGURE 9B
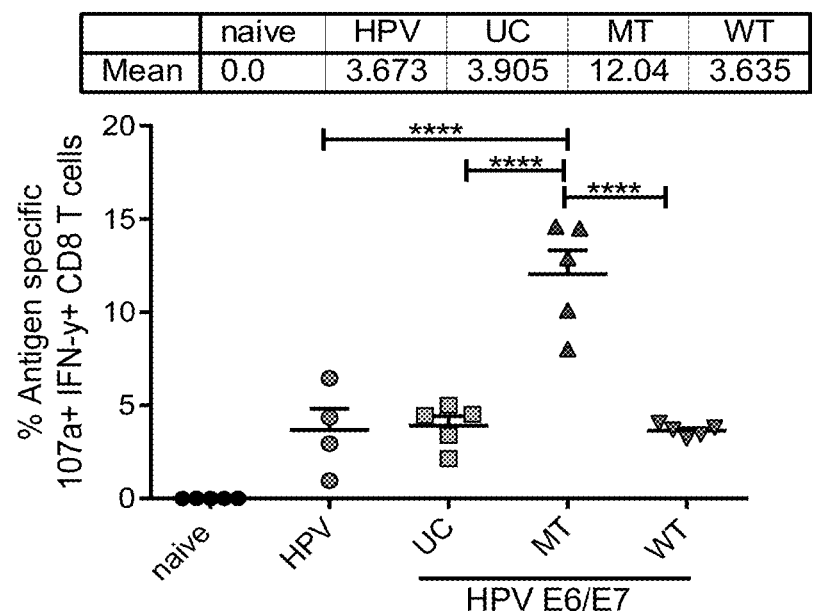
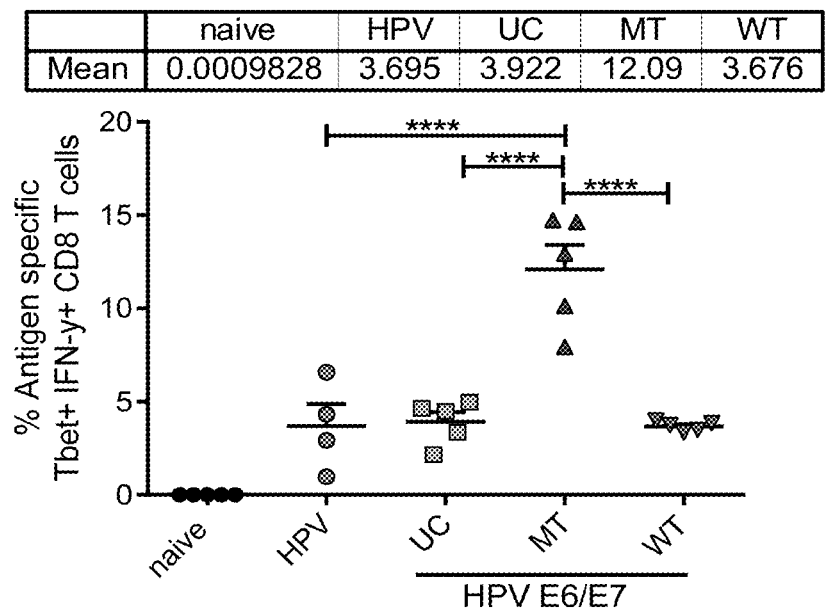
FIGURE 9 (cont.)

FIGURE 9D
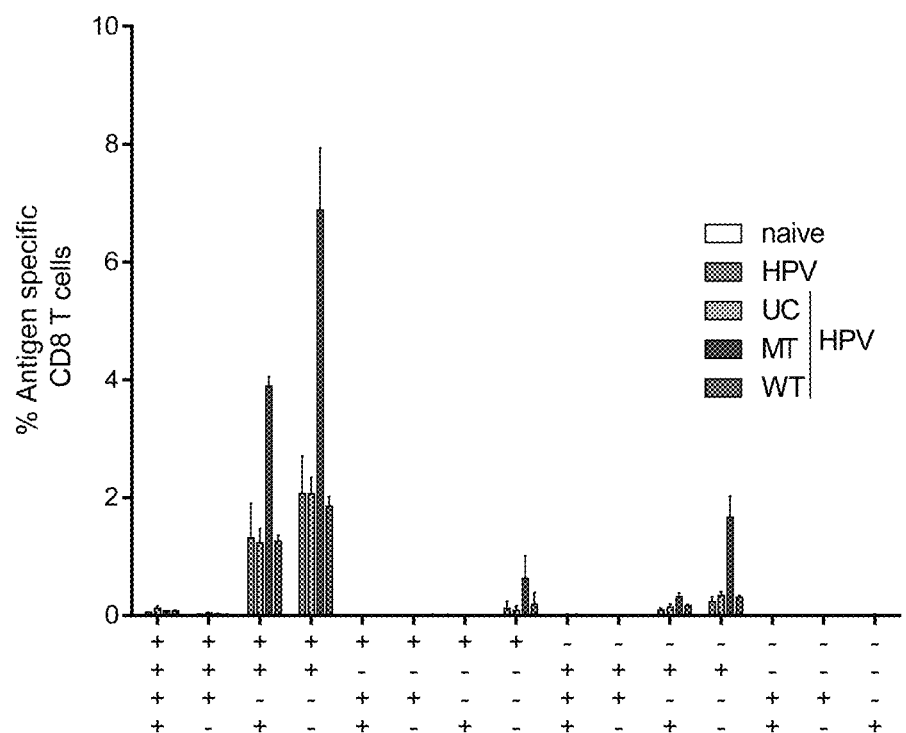
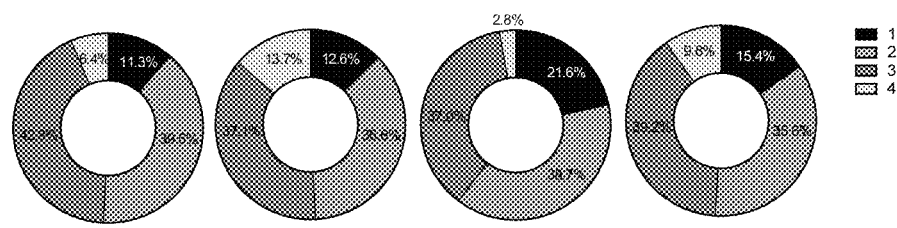
FIGURE 9 (cont.)

FIGURE 10A
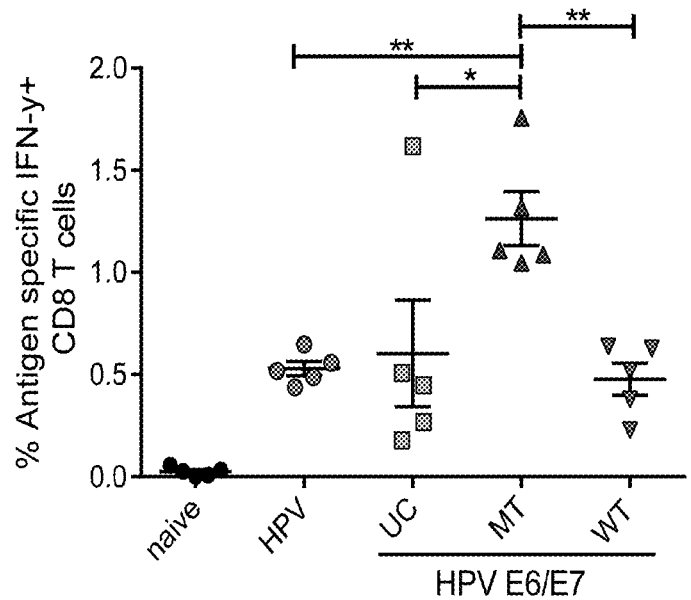
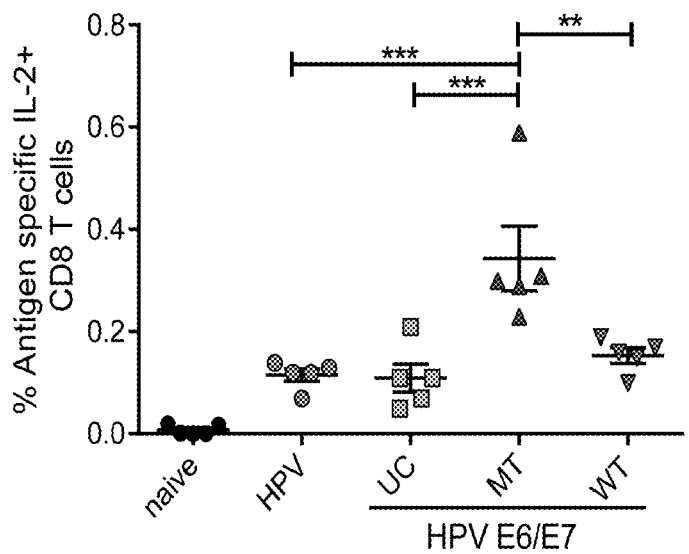
FIGURE 10

FIGURE 10B
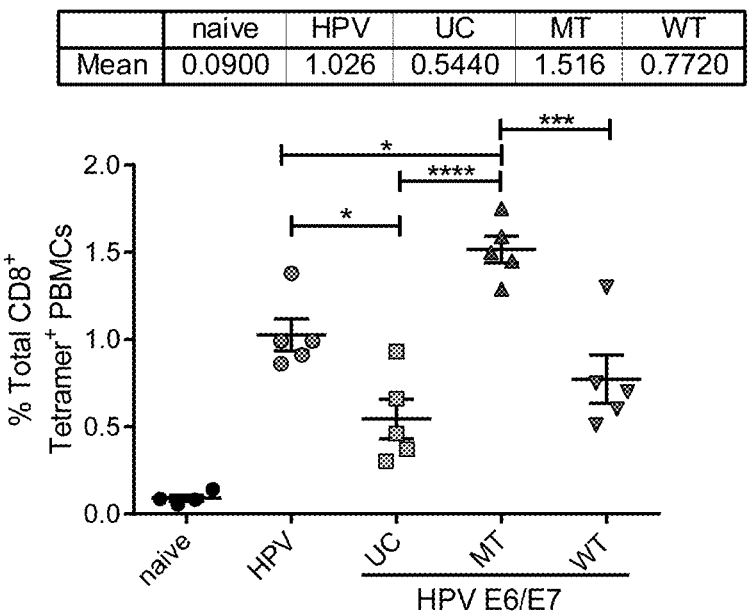
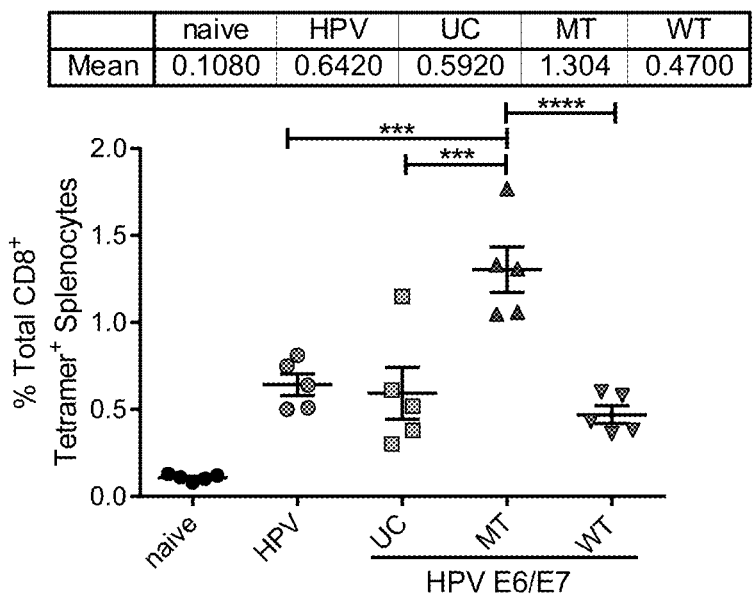
FIGURE 10 (cont.)

FIGURE 11A
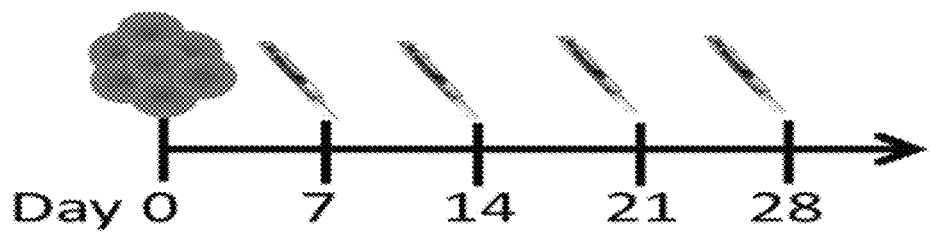
FIGURE 11B
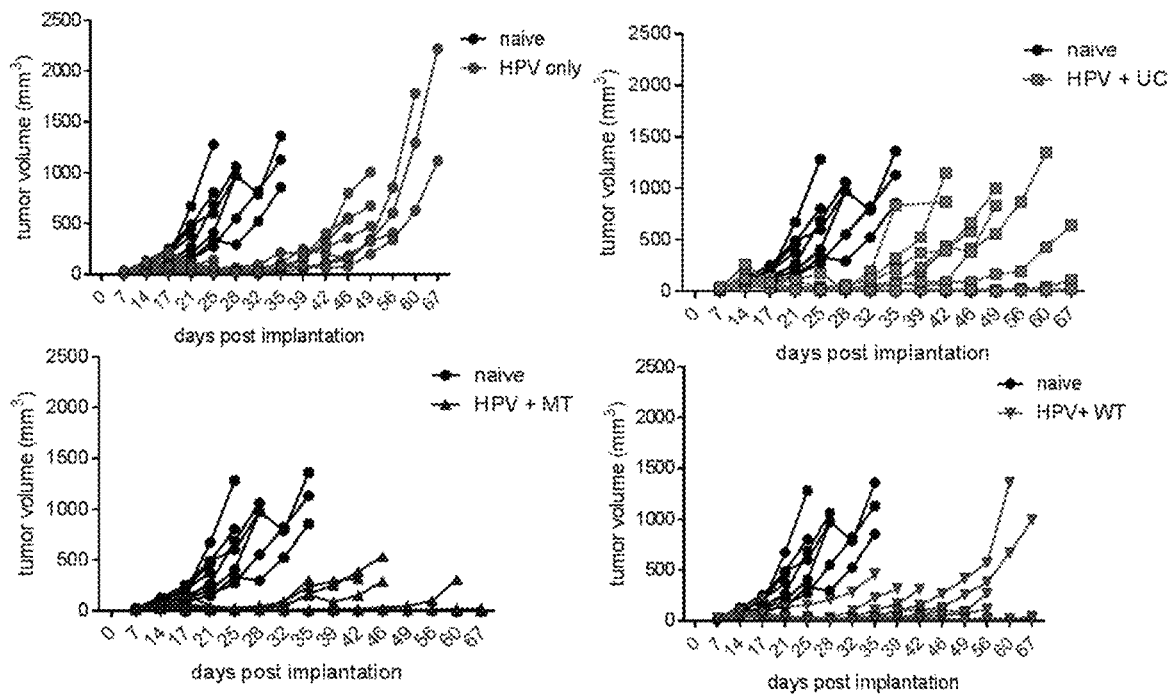
FIGURE 11

FIGURE 12A
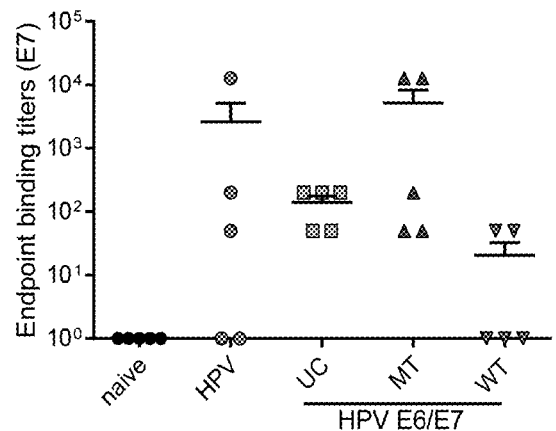
FIGURE 12B
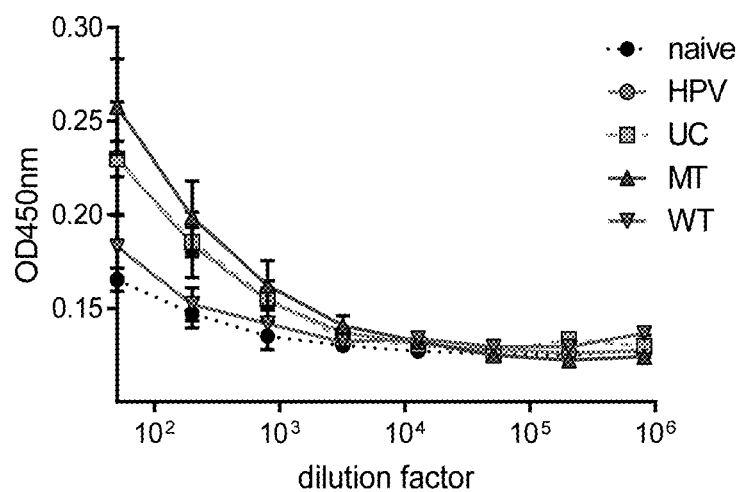
FIGURE 12

SEQUENCE LISTING

<160> NUMBER OF SEQ ID NOS: 14

<210> SEQ ID NO 1
<211> LENGTH: 789
<212> TYPE: DNA
<213> ORGANISM: Artificial Sequence
<220> FEATURE:
<223> OTHER INFORMATION: Human wtCD40L DNA

<400> SEQUENCE: 1

```
atgattgaaa cctacaacca gacctcacct cgctccgctg ccacaggact gcccattagt      60
atgaaaatct ttatgtatct gctgacagtc ttcctgatca cccagatgat tggcagcgcc     120
ctgtttgcag tgtacctgca ccggagactg gacaagatcg aggatgaacg caacctgcat     180
gaggacttcg tgtttatgaa aacaattcag cgatgcaaca ctggagaacg gtccctgtct     240
ctgctgaatt gtgaggaaat caagtcccag ttcgagggct tgtgaagga cattatgctg      300 aacaaagagg aaacaaagaa agagaactct ttcgaaatgc agaaagggga tcagaatcct     360
cagatcgccg ctcacgtcat ttctgaggcc agctccaaga ccacaagtgt gctgcagtgg     420
gctgaaaaag gatactatac catgagtaac aatctggtca cactggaaaa cgggaagcag     480
ctgactgtga aaagacaggg actgtactat atctatgctc aggtgacctt ctgcagcaat     540
agggaggcct ctagtcaggc tcccttatc gcaagcctgt gcctgaagtc ccctggcagg     600
ttcgaacgca ttctgctgcg agcagccaac acacactcaa gcgcaaaacc ctgcggccag     660
cagtcaattc atctgggagg agtcttcgag ctgcagccaa gagccagcgt gtttgtcaat     720
gtgactgatc ccagtcaggt gtcacatgga actggcttca cctcctttgg gctgctgaag     780
ctgtgatga                                                             789
```

<210> SEQ ID NO 2
<211> LENGTH: 261
<212> TYPE: PRT
<213> ORGANISM: Artificial Sequence
<220> FEATURE:
<223> OTHER INFORMATION: Human wtCD40L protein

<400> SEQUENCE: 2

```
Met Ile Glu Thr Tyr Asn Gln Thr Ser Pro Arg Ser Ala Ala Thr Gly
  1               5                  10                  15

Leu Pro Ile Ser Met Lys Ile Phe Met Tyr Leu Leu Thr Val Phe Leu
             20                  25                  30

Ile Thr Gln Met Ile Gly Ser Ala Leu Phe Ala Val Tyr Leu His Arg
         35                  40                  45

Arg Leu Asp Lys Ile Glu Asp Glu Arg Asn Leu His Glu Asp Phe Val
     50                  55                  60

Phe Met Lys Thr Ile Gln Arg Cys Asn Thr Gly Glu Arg Ser Leu Ser
```

```
                65                  70                  75                  80
Leu Leu Asn Cys Glu Glu Ile Lys Ser Gln Phe Glu Gly Phe Val Lys
                    85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
                115                 120                 125

Glu Ala Ser Ser Lys Thr Thr Ser Val Leu Gln Trp Ala Glu Lys Gly
            130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Gln Ala Pro Phe Ile Ala Ser
                180                 185                 190

Leu Cys Leu Lys Ser Pro Gly Arg Phe Glu Arg Ile Leu Leu Arg Ala
                195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 453
<212> TYPE: DNA
<213> ORGANISM: Artificial Sequence
<220> FEATURE:
<223> OTHER INFORMATION: Human mCD40L DNA

<400> SEQUENCE: 3
atgcagaagg gagatcagaa tccccagatc gccgctcatg tcattagcga ggctagctcc      60
aagaccacat ccgtgctgca gtgggcagaa aaaggctact atacaatgtc aacaatctg     120 gtcactctgg aaaacggaaa gcagctgacc gtgaaacgac agggcctgta ctatatctac     180
gcccaggtga cattctgcag caatagagag gcttctagtc aggcacccct tatcgccagt     240
ctgtgcctga gtcacctggc ggttcgaa agaattctgc tgcgggcagc caacactcac     300
tcaagcgcca aaccatgcgg gcagcagtct attcatctgg gaggggtgtt cgagctgcag     360
ccaggagcta gcgtgttcgt caatgtgacc gacccatcac aggtgtctca cgggactggc     420
ttcacatcat ttggactgct gaaactgtga tga                                  453

<210> SEQ ID NO 4
<211> LENGTH: 149
<212> TYPE: PRT
<213> ORGANISM: Artificial Sequence
<220> FEATURE:
<223> OTHER INFORMATION: Human mCD40L protein

<400> SEQUENCE: 4

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
                20                  25                  30
```

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
 50                  55                  60

Phe Cys Ser Asn Arg Glu Ala Ser Ser Gln Ala Pro Phe Ile Ala Ser
 65                  70                  75                  80

Leu Cys Leu Lys Ser Pro Gly Arg Phe Glu Arg Ile Leu Leu Arg Ala
                 85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
            115                 120                 125

Val Thr Asp Pro Ser Gln Val Ser His Gly Thr Gly Phe Thr Ser Phe
130                 135                 140

Gly Leu Leu Lys Leu
145

<210> SEQ ID NO 5
<211> LENGTH: 768
<212> TYPE: DNA
<213> ORGANISM: Artificial Sequence
<220> FEATURE:
<223> OTHER INFORMATION: Human ucCD40L DNA

<400> SEQUENCE: 5

```
atgattgaaa cctacaacca gacctcacct cgctccgctg ccacaggact gcccattagt      60
atgaaaatct ttatgtatct gctgacagtc ttcctgatca cccagatgat tggctccgct     120
ctgtttgcag tgtacctgca ccggagactg acaagatcg aggatgaacg caacctgcat     180
gaggacttcg tgtttatgaa acaattcag cgatgcaaca ctggagaacg gtccctgtct     240
ctgctgaatt gtgaggaaat caagtcccag ttcgagggct tgtgtaagga cattatgctg     300
aacaaagagg aaacaaagaa agagaacgat cagaatcctc agatcgccgc tcacgtcatt     360
tctgaggcca gctccaagac cacaagtgtg ctgcagtggg ctgaaaaagg atactatacc     420
atgagtaaca atctggtcac actggaaaac gggaagcagc tgactgtgaa agacaggga      480
ctgtactata tctatgctca ggtgaccttc tgcagcaata gggaggcctc tagtcaggct     540
ccctttatcg caagcctgtg cctgaagtcc cctggcaggt tcgaacgcat tctgctgcga     600
gcagccaaca cacactcaag cgcaaaaccc tgcggccagc agtcaattca tctgggagga     660
gtcttcgagc tgcagccagg agccagcgtg tttgtcaatg tgactgatcc cagtcaggtg     720
tcacatggaa ctggcttcac ctcctttggg ctgctgaagc tgtgatga                  768
```

<210> SEQ ID NO 6
<211> LENGTH: 254
<212> TYPE: PRT
<213> ORGANISM: Artificial Sequence
<220> FEATURE:
<223> OTHER INFORMATION: Human ucCD40L protein

<400> SEQUENCE: 6

Met Ile Glu Thr Tyr Asn Gln Thr Ser Pro Arg Ser Ala Ala Thr Gly
 1               5                  10                  15

Leu Pro Ile Ser Met Lys Ile Phe Met Tyr Leu Leu Thr Val Phe Leu
             20                  25                  30

Ile Thr Gln Met Ile Gly Ser Ala Leu Phe Ala Val Tyr Leu His Arg
         35                  40                  45

```
Arg Leu Asp Lys Ile Glu Asp Glu Arg Asn Leu His Glu Asp Phe Val
         50                  55                  60
Phe Met Lys Thr Ile Gln Arg Cys Asn Thr Gly Glu Arg Ser Leu Ser
 65                  70                  75                  80
Leu Leu Asn Cys Glu Glu Ile Lys Ser Gln Phe Glu Gly Phe Val Lys
                 85                  90                  95
Asp Ile Met Leu Asn Lys Glu Glu Thr Lys Lys Glu Asn Asp Gln Asn
            100                 105                 110
Pro Gln Ile Ala Ala His Val Ile Ser Glu Ala Ser Ser Lys Thr Thr
            115                 120                 125
Ser Val Leu Gln Trp Ala Glu Lys Gly Tyr Tyr Thr Met Ser Asn Asn
            130                 135                 140
Leu Val Thr Leu Glu Asn Gly Lys Gln Leu Thr Val Lys Arg Gln Gly
145                 150                 155                 160
Leu Tyr Tyr Ile Tyr Ala Gln Val Thr Phe Cys Ser Asn Arg Glu Ala
                165                 170                 175
Ser Ser Gln Ala Pro Phe Ile Ala Ser Leu Cys Leu Lys Ser Pro Gly
            180                 185                 190
Arg Phe Glu Arg Ile Leu Leu Arg Ala Ala Asn Thr His Ser Ser Ala
            195                 200                 205
Lys Pro Cys Gly Gln Gln Ser Ile His Leu Gly Gly Val Phe Glu Leu
            210                 215                 220
Gln Pro Gly Ala Ser Val Phe Val Asn Val Thr Asp Pro Ser Gln Val
225                 230                 235                 240
Ser His Gly Thr Gly Phe Thr Ser Phe Gly Leu Leu Lys Leu
                245                 250
```

<210> SEQ ID NO 7
<211> LENGTH: 783
<212> TYPE: DNA
<213> ORGANISM: Artificial Sequence
<220> FEATURE:
<223> OTHER INFORMATION: Mouse wtCD40L DNA

<400> SEQUENCE: 7

```
atgatcgaaa cttattccca gccttcccct cggtccgtcg ccacaggtct gccagcctca    60
atgaaaatct ttatgtatct cctcactgtg ttcctgatca cccagatgat tggcagcgtc   120
ctgtttgctg tgtacctgca caggagactc gacaaggtcg aggaagaagt gaatctgcat   180
gaagatttcg tgtttatcaa gaaactgaag cgctgcaaca aggggagggt tcactgagc    240
ctgctcaatt gtgaagagat gcggcgccag ttcgaggacc tggtgaagga tatcacactc   300
aacaagaag agaagaaaga aaactccttc gagatgcagc gaggggacga agatccacag    360
attgccgctc acgtggtctc cgaggcaaac tctaatgcag ccagtgtgct gcagtgggcc   420
aagaaaggtt actatactat gaagagtaac ctggtcatgc tcgaaaatgg caagcagctg   480
accgtgaaaa gagagggact ctactatgtc tatacccagg tgacattctg cagcaaccga   540
gaacccagct cccagaggcc ttttatcgtg gggctgtggc tcaagccctc tagtggttcc   600
gagcggattc tgctcaaagc tgcaaataca cactcaagct cccagctgtg tgaacagcag   660
tctgtccatc tgggaggagt gttcgagctc caggcaggag cttcagtgtt tgtcaacgtg   720
actgaggcca gccaggtcat tcatcgggtg ggcttctcta gttttggact gctcaagctg   780
tag                                                                  783
```

```
<210> SEQ ID NO 8
<211> LENGTH: 260
<212> TYPE: PRT
<213> ORGANISM: Artificial Sequence
<220> FEATURE:
<223> OTHER INFORMATION: Mouse wtCD40L protein

<400> SEQUENCE: 8
```

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

```
<210> SEQ ID NO 9
<211> LENGTH: 441
<212> TYPE: DNA
<213> ORGANISM: Artificial Sequence
<220> FEATURE:
<223> OTHER INFORMATION: Mouse mCD40L DNA

<400> SEQUENCE: 9
```
atggatgaag accccagat tgccgcacac gtcgtcagcg aagctaactc aaacgccgcc      60
tccgtcctcc agtgggctaa gaagggatac tatactatga gagtaacct ggtcatgctg     120 gagaatggga agcagctgac cgtgaaacgg gaaggtctgt actatgtcta cacccaggtg     180
acattctgct ctaacaggga gcccagctcc cagagaccctt ttatcgtggg cctgtggctc    240
aagccatcta gtggcagcga acgcattctg ctcaaagccg ctaatacaca ctcaagctcc    300

```
cagctgtgtg agcagcagtc tgtccatctg gcggagtgt cgaactcca ggcaggggcc      360 tcagtgtttg tcaacgtgac cgaggctagc caggtcatcc acagggtggg gttctctagt    420
tttggtctgc tcaaactgta g                                              441
```

<210> SEQ ID NO 10
<211> LENGTH: 146
<212> TYPE: PRT
<213> ORGANISM: Artificial Sequence
<220> FEATURE:
<223> OTHER INFORMATION: Mouse mCD40L protein

<400> SEQUENCE: 10

```
Met Asp Glu Asp Pro Gln Ile Ala Ala His Val Val Ser Glu Ala Asn
1               5                   10                  15

Ser Asn Ala Ala Ser Val Leu Gln Trp Ala Lys Lys Gly Tyr Tyr Thr
            20                  25                  30

Met Lys Ser Asn Leu Val Met Leu Glu Asn Gly Lys Gln Leu Thr Val
        35                  40                  45

Lys Arg Glu Gly Leu Tyr Tyr Val Tyr Thr Gln Val Thr Phe Cys Ser
    50                  55                  60

Asn Arg Glu Pro Ser Ser Gln Arg Pro Phe Ile Val Gly Leu Trp Leu
65                  70                  75                  80

Lys Pro Ser Ser Gly Ser Glu Arg Ile Leu Leu Lys Ala Ala Asn Thr
                85                  90                  95

His Ser Ser Ser Gln Leu Cys Glu Gln Gln Ser Val His Leu Gly Gly
            100                 105                 110

Val Phe Glu Leu Gln Ala Gly Ala Ser Val Phe Val Asn Val Thr Glu
        115                 120                 125

Ala Ser Gln Val Ile His Arg Val Gly Phe Ser Ser Phe Gly Leu Leu
    130                 135                 140

Lys Leu
145
```

<210> SEQ ID NO 11
<211> LENGTH: 762
<212> TYPE: DNA
<213> ORGANISM: Artificial Sequence
<220> FEATURE:
<223> OTHER INFORMATION: Mouse ucCD40L DNA

<400> SEQUENCE: 11

```
atgattgaaa cttactcaca gccctcccct cggtccgtcg caactggtct gcctgcctcc     60
atgaaaatct ttatgtatct cctgactgtg ttcctgatca cccagatgat tggcagcgtc    120
ctgtttgctg tgtacctgca caggagactc gacaaggtcg aggaagaagt gaatctgcat    180
gaagatttcg tgtttatcaa gaaactgaag cgctgcaaca agggggaggg ttcactgagc    240
ctgctcaatt gtgaagagat gcggcgccag ttcgaagacc tggtgaagga tatcacactc    300
aacaaagaag agaagaaaga aaatgacgag gacccccaga ttgccgctca cgtggtctcc    360
gaggcaaact ctaatgcagc cagtgtgctg cagtgggcca agaaagggta ctatactatg    420
aagagtaacc tggtcatgct cgaaaatggc aagcagctga ccgtgaaaag agagggactc    480
tactatgtct atacccaggt gacattctgc agcaaccgag aacccagctc ccagaggcct    540
tttatcgtgg ggctgtggct caagccctct agtggttccg agcggattct gctcaaagct    600
gcaaatacac actcaagctc ccagctgtgt gaacagcagt ctgtccatct gggaggagtg    660
```

```
ttcgagctcc aggcaggtgc ttcagtgttt gtcaacgtga ctgaggccag ccaggtcatt    720
catagagtgg gcttctctag ttttggactg ctcaagctgt ag                      762
```

<210> SEQ ID NO 12
<211> LENGTH: 253
<212> TYPE: PRT
<213> ORGANISM: Artificial Sequence
<220> FEATURE:
<223> OTHER INFORMATION: Mouse ucCD40L protein

<400> SEQUENCE: 12

```
Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65              70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Asp Glu Asp Pro
            100                 105                 110

Gln Ile Ala Ala His Val Val Ser Glu Ala Asn Ser Asn Ala Ala Ser
        115                 120                 125

Val Leu Gln Trp Ala Lys Lys Gly Tyr Tyr Thr Met Lys Ser Asn Leu
    130                 135                 140

Val Met Leu Glu Asn Gly Lys Gln Leu Thr Val Lys Arg Glu Gly Leu
145                 150                 155                 160

Tyr Tyr Val Tyr Thr Gln Val Thr Phe Cys Ser Asn Arg Glu Pro Ser
                165                 170                 175

Ser Gln Arg Pro Phe Ile Val Gly Leu Trp Leu Lys Pro Ser Ser Gly
            180                 185                 190

Ser Glu Arg Ile Leu Leu Lys Ala Ala Asn Thr His Ser Ser Ser Gln
        195                 200                 205

Leu Cys Glu Gln Gln Ser Val His Leu Gly Gly Val Phe Glu Leu Gln
    210                 215                 220

Ala Gly Ala Ser Val Phe Val Asn Val Thr Glu Ala Ser Gln Val Ile
225                 230                 235                 240

His Arg Val Gly Phe Ser Ser Phe Gly Leu Leu Lys Leu
                245                 250
```

<210> SEQ ID NO 13
<211> LENGTH: 471
<212> TYPE: DNA
<213> ORGANISM: Artificial Sequence
<220> FEATURE:
<223> OTHER INFORMATION: macaca MT CD40L DNA

<400> SEQUENCE: 13

```
ggatccgcca ccatgcagaa gggagaccag aaccctcaga tcgccgctca cgtcatttcc    60
gaggcttcca gcaagaccac aagcgtgctg cagtgggcag aaaaaggcta ctatacaatg   120
tctaacaatc tggtgaccct ggagaacggg aagcagctga ccgtgaaacg cagggactc    180 tactatatct acgcccaggt gacattctgc tccaatcgcg aggcttctag tcaggcaccc   240
```

```
tttatcgcca gtctgtgcct caagtcacct gggaggttcg aaagaattct gctcagggca    300
gccaacactc actcatccgc taaaccctgc ggccagcagt ctattcatct gggcggggtc    360
ttcgaactcc agccaggagc ctccgtgttc gtcaatgtga cagatcccag ccaggtgtct    420
catggaactg gcttcaccag ctttggcctg ctcaaactgt gataactcga g             471

<210> SEQ ID NO 14
<211> LENGTH: 149
<212> TYPE: PRT
<213> ORGANISM: Artificial Sequence
<220> FEATURE:
<223> OTHER INFORMATION: macaca MT CD40L protein

<400> SEQUENCE: 14

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
                20                  25                  30

Tyr Tyr Thr Met Ser Asn Asn Leu Val Thr Leu Glu Asn Gly Lys Gln
            35                  40                  45

Leu Thr Val Lys Arg Gln Gly Leu Tyr Tyr Ile Tyr Ala Gln Val Thr
        50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145
```

VACCINES WITH CD40 LIGAND AS AN ADJUVANT

CROSS-REFERENCE TO RELATED APPLICATIONS

This application is the U.S. national stage application filed under 35 U.S.C. § 371 claiming benefit to International Patent Application No. PCT/US2016/023126, filed Mar. 18, 2016, which claims priority to U.S. Provisional Application No. 62/136,283, filed Mar. 20, 2015 and U.S. Provisional Application No. 62/303,984, filed Mar. 4, 2016, which are hereby incorporated by reference in their entirety.

TECHNICAL FIELD

The present invention relates to vaccines comprising an antigen and CD40L, and methods of administering such vaccines.

BACKGROUND

Vaccines are used to stimulate an immune response in an individual to provide protection against and/or treatment for a particular disease. Some vaccines include an antigen to induce the immune response. Some antigens elicit a strong immune response while other antigens elicit a weak immune response. A weak immune response to an antigen can be strengthened by including an adjuvant in the vaccine. Adjuvants come in many different forms, for example, aluminum salts, oil emulsions, sterile constituents of bacteria or other pathogens, cytokines, and so forth.

Cytokines are proteins made by cells that affect the behavior of other cells, and unlike many adjuvants, can modulate specific immune responses. One such cytokine is CD40, which is a costimulatory molecule found on antigen presenting cells, including B cells. The CD40 protein is a receptor on antigen-presenting cells of the immune system and is essential for mediating a broad variety of immune responses. CD40 ligand is found on the surface of T cells, and attaches to its receptor protein, CD40. When the CD40 receptor and CD40 ligand interact a series of chemical signals is triggered instructing B cells to produce antibodies. CD40 ligand also plays a role in allowing T-cells to interact with other cells of the immune system and plays a role in T-cell differentiation. Vaccines are also administered in many different ways (e.g., injection, orally, etc.) into many different tissues (e.g., intramuscular, intradermal, etc.). Not all delivery methods, however, are equal. Some delivery methods allow for greater compliance within a population of individuals while other delivery methods may affect the immunogenicity and/or safety of the vaccine. Accordingly, a need remains in the art for the development of safe and more effective adjuvants that increase antigenic responses irrespective of the identity of the antigen and route of administration.

SUMMARY OF THE INVENTION

The present invention is directed to a vaccine comprising an antigen and CD40L wherein the antigen may be encoded by a first nucleic acid and CD40L may be encoded by a second nucleic acid. In preferred embodiments, the CD40L is comprised of nucleotide sequence having at least about 90% identity to a nucleotide sequence as set forth in SEQ ID NOS: 1, 3, 5, 7, 9, 11 or 13; and in some preferred embodiments the CD40L is comprised of nucleotide sequence SEQ ID NO: 1 or SEQ ID NO: 3.

The first and second nucleic acids of the vaccine may further comprise an expression vector. The vaccine can further comprise an antigen peptide with the same sequence encoded by the nucleic acid sequence of the above antigen, and a CD40L peptide with the same sequence encoded by the nucleic acid sequence as the above CD40L. The antigen of the vaccine is selected from a group consisting of a human papilloma virus (HPV) antigen, an HIV antigen, an influenza antigen, a *Plasmodium falciparum* antigen, or fragment thereof. The HPV antigen can be selected from the group consisting of HPV16 E6 antigen, an HPV16 E7 antigen and combination thereof. The HIV antigen can be selected from the group consisting of Env A, Env B, Env C, Env D, B Nef-Rev, Gag, and any combination thereof. The influenza antigen is selected from the group consisting of H1 HA, H2 HA, H3 HA, H5 HA, BHA antigen and combination thereof. The *Plasmodium falciparum* antigen may include a circumsporozoite (CS) antigen.

The vaccine can further comprise a pharmaceutically acceptable excipient. The second nucleic acid can further comprise an expression vector.

The present invention is further directed to a method for increasing an immune response in a subject, the method comprising administering a vaccine of described herein to the subject in need thereof, wherein administering the vaccine includes at least one of intramuscular administration and intradermal administration. The vaccine can also be administered through electroporation. The method increases immune response in at least one of a skin tissue and a muscle tissue of the subject, and increases the immune response in the subject by about 10% to about 600%, or by about 10% to about 250%. The method of vaccination with the CD40L adjuvant vaccine may increase the immune response in the subject in need thereof by at least about 1.20-fold or at least about 1.5 fold.

BRIEF DESCRIPTION OF THE DRAWINGS

FIG. 1 shows (A) a diagram of different CD40L isoforms. The mouse sequence was used followed by additional modifications to create the variant isoforms. Each insert was RNA and codon optimized and includes an efficient IgE leader sequence; and were then cloned into the pVAX vector where expression was controlled under a CMV promoter; (B) a Western blot analysis of cell lysate from 293T transfected cells.

FIG. 3 shows (A) an immunization schedule (immunized twice followed by an 8 week rest before sacrificing); (B) endpoint binding titers to consensus clade c gp120 (determined during memory phase); and (C) splenocytes isolated from vaccinated mice stimulated following by intracellular staining.

FIG. 4 shows (A) an immunization schedule, immunized twice with either HPV 16 E6/E7 DNA alone or in combination with one of the CD40L isoforms; (B) ELISpot determination of IFN-γ production one week after final vaccination; (C) splenocytes isolated from vaccinated mice stimulated with E7/E6 peptides following by intracellular staining; and (D) mice were implanted with 5×10⁴ TC 1 cells on day 0. On days 4, 11, 18 and 25 mice were vaccinated; and (E) tumor measurements were taken every week following implantation.

FIG. 6 shows (A) diagram of different CD40L isoforms. The mouse sequence was used followed by additional modifications to create a WT form, an uncleavable form (only expressed on the surface) and a soluble mature form. Each insert was RNA and codon optimized; and were then cloned into the pVAX vector where expression is controlled under a human CMV promoter; (B) Western blot analysis of cell lysate from 293T transfected cells.

DETAILED DESCRIPTION

Figures 2, 2C:
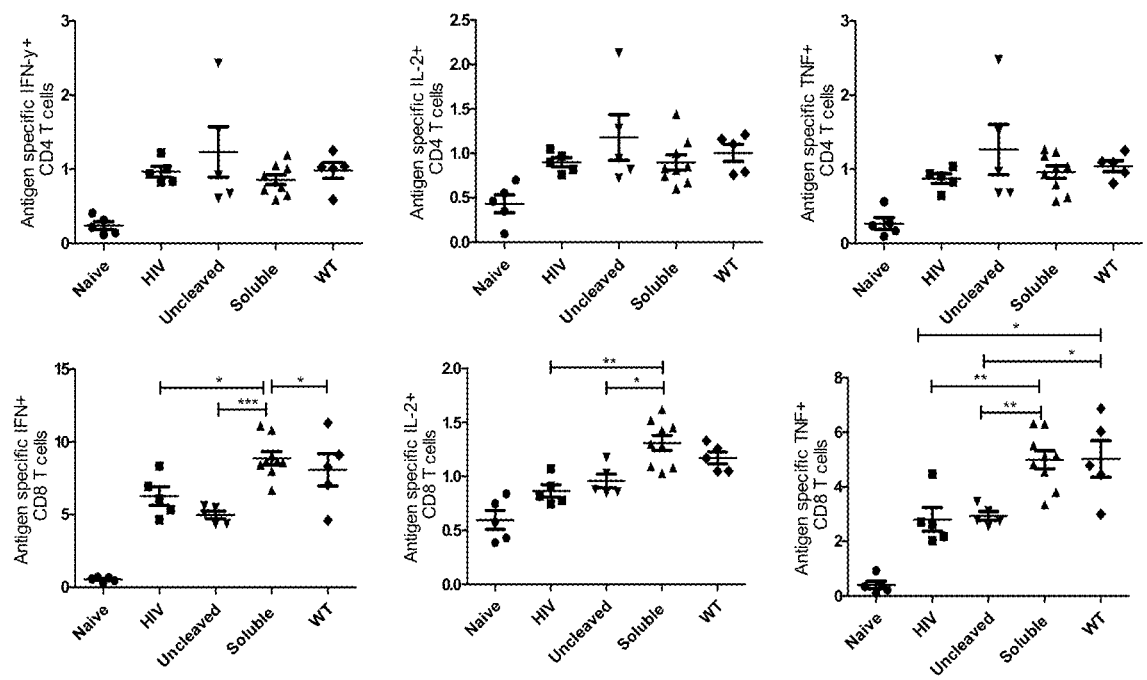
FIG. 2 shows (A) an immunization schedule (immunized every 3 weeks with either HIV consensus clade c envelope alone (2.5μ) or in combination with the different forms of CD40L); (B) endpoint binding titers to consensus clade c gp120 determined 1 week after vaccination; and (C) a measurement of IFN-γ, IL-2, and TNF-α cytokine production from antigen specific CD4+ and CD8+ T cells following immunization with HIV envelope consensus clade c, specifically, splenocytes isolated from vaccinated mice stimulated for 5 hours with peptides following by intracellular staining.

The present invention relates to vaccines that can be used to increase an immune response to an antigen in a subject by using CD40L as an adjuvant.

In some instances, CD40L can function as a universal adjuvant because a greater immune response is elicited in the subject regardless of the source of the antigen or the route of administration as compared to a vaccine comprising the antigen alone. CD40L may further augment the immune response of both viral and parasite antigens, for example, a human papilloma virus (HPV) antigen and a *Plasmodium falciparum* antigen, respectively. In some instances, CD40L can further augment the immune response in both muscle and skin tissues as demonstrated by increased interferon-γ (IFN-γ), tumor necrotic factor alpha (TNF-α) and interleukin-2 (IL-2) production.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Adjuvant" as used herein means any molecule added to the vaccines described herein to enhance the immunogenicity of the antigens.

"Fragment" as used herein means a nucleic acid sequence or a portion thereof, that encodes a polypeptide capable of eliciting an immune response in a mammal. The fragments can be DNA fragments selected from at least one of the various nucleotide sequences that encode protein fragments set forth below.

"Immune response" as used herein means the activation of a host's immune system, e.g., that of a mammal, in response to the introduction of antigen. The immune response can be in the form of a cellular or humoral response, or both.

"Nucleic acids" as used herein can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

A "peptide," "protein," or "polypeptide" as used herein can mean a linked sequence of amino acids and can be natural, synthetic, or a modification or combination of natural and synthetic.

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Treatment" or "treating," as used herein can mean protecting of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Subject" as used herein can mean a mammal that wants to or is in need of being immunized with the herein described vaccines. The can be a human, chimpanzee, dog, cat, horse, cow, mouse, or rat.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Variant can further be defined as a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein means a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

2. Vaccines

Provided herein is a vaccine comprising an antigen and an adjuvant. The vaccine can increase antigen presentation and the overall immune response to the antigen in an individual. The combination of antigen and adjuvant induces the immune system more efficiently than a vaccine comprising the antigen alone. The vaccine can further induce an immune response when administered to different tissues such as the muscle and the skin.

The vaccine of the present invention can have features required of effective vaccines such as being safe so the vaccine itself does not cause illness or death; protective again illness resulting from exposure to live pathogens such as viruses or bacteria; induces neutralizing antibody to prevent infection of cells; induces protective T cell against intracellular pathogens; and provides a ease of administration, few side effects, biological stability, and low cost per dose. The vaccine can accomplish some or all of these features by combining the antigen with the adjuvant as discussed below.

a. Adjuvant

The vaccine can comprise an adjuvant. The adjuvant can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the adjuvant by a peptide bond. The amino acid sequence can be a protein, a peptide, a variant thereof, a fragment thereof, or a combination thereof.

(1) CD40L

The adjuvant can be CD40 ligand (CD40L), fragments thereof, variants thereof, or the combination thereof. CD40L (also known as CD154) is expressed by activated T cells and serves as an activating ligand that may induce a number of different effects in the responding cell. CD40L, as expressed by activated T-cells, is synthesized within the cell cytoplasm and transported to the surface of the cell, where it is inserted into the cell membrane. After insertion, this protein is cleaved off of the cell surface by associated enzymes and remains biologically active in its soluble form. Due to its role in both innate and adaptive immunity, the co-delivery of pCD40L could increase vaccine responses in a DNA vaccine setting.

CD40L can stimulate IFN-γ production. IFN-γ has anti-viral, immunoregulatory, and anti-tumor properties and can alter transcription in up to 30 genes producing a variety of physiological and cellular responses. These effects include promoting natural killer cell (NK cells) activity, causing normal cells to increase expression of class I MHC molecules, increasing antigen presentation and lysosome activity in macrophages, inducing nitric oxide synthase (iNOS), promoting Th1 differentiation to cellular immunity regarding cytotoxic CD8+ T cells while suppressing Th2 differentiation in humoral (antibody) response. Inclusion of CD40L in the vaccine can induce IFN-γ production by at least about 1.20-fold, at least about 1.5-fold, at least about 2-fold, at least about 3-fold, at least about 4-fold, at least about 5-fold, at least about 8-fold, and at least about 10-fold as compared to a vaccine not including CD40L. Inclusion of CD40L in the vaccine can induce IFN-γ production by at least about 1.20-fold as compared to a vaccine not including CD40L. Inclusion of CD40L in the vaccine can also induce IL-2 production by at least about at least about 1.25-fold, at least about 1.5-fold, at least about 2-fold, at least about 3-fold, at least about 4-fold as compared to a vaccine not including CD40L. Inclusion of CD40L in the vaccine can also induce TNF-α production by at least about at least about 1.5-fold, at least about 2-fold, at least about 3-fold, at least about 4-fold, at least about 5-fold, at least about 8-fold, and at least about 10-fold as compared to a vaccine not including CD40L. CD40L can increase or boost the immune response to the antigen in a subject. The antigen is discussed in more detail below. In some instances, CD40L can increase the immune response to the antigen by about 10% to about 500%. Alternatively, CD40L can increase the immune response to the antigen may be increased by about 10% to about 250%. In still other alternative embodiments, CD40L can increase the immune response to the antigen may be increased by at least about 10%, 20%, 30%, 40%, 50%, 60%, 70%, 80%, 90%, 100%, 110%, 120%, 130%, 140%, 150%, 160%, 170%, 180%, 190%, 200%, 220%, 230%, 240%, 250%, 260%, 270%, 280%, 290%, 300%, 310%, 320%, 330%, 340%, 350%, 360%, 370%, 380%, 390%, 400%, 410, 420%, 430%, 440%, 450%, 460%, 470%, 480%, 490%, 500%, 510%, 520%, 530%, 540%, 550%, 560%, 570%, 580%, 590% or 600%.

In other embodiments, CD40L can increase or boost the immune response to a particular antigen from a vaccine that is administered to a subject in need thereof by at least about 1.2-fold, at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

A nucleic acid encoding CD40L can be from any number of organisms, for example, mouse (*Mus musculus*), macaque (*Macacac mulatta*), and human (*Homo sapiens*). The nucleic acid encoding CD40L can be optimized with regards to codon usage and corresponding RNA transcripts. The nucleic acid encoding CD40L can be a codon and RNA optimized for expression. The nucleic acid encoding CD40L can also include a nucleotide sequence encoding an IgE leader sequence. The IgE leader sequence can be located 5' to CD40L in the nucleic acid. In some embodiments, the nucleic acid encoding CD40L is free of or does not contain a nucleotide sequence encoding the IgE leader sequence.

The mouse CD40L can be the optimized nucleic acid sequence SEQ ID NOS: 7, 9 and/or 11, which encode for SEQ ID NOS: 8, 10 and/or 12, respectively. In some embodiments the mouse CD40L can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence as set forth in SEQ ID NOS:7, 9 and/or 11. The mouse CD40L can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence as set forth in SEQ ID NOS: 8, 10 and/or 12.

The macaque CD40L can be the optimized nucleic acid sequence SEQ ID NO: 13, which encodes SEQ ID NO: 14, respectively. In some embodiments the macaque CD40L can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence as set forth in SEQ ID NO: 13. The macaque CD40L can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence as set forth in SEQ ID NO: 14.

The human CD40L can be optimized nucleic acid sequence SEQ ID NOS: 1, 3, and/or 5, which encode for SEQ ID NOS: 2, 4 and/or 6, respectively. In some embodiments, the human CD40L can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the nucleic acid sequence as set forth in SEQ ID NOS: 1, 3 and/or 5. In other embodiments, the human CD40L sequence can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or 100% identity over an entire length of the amino acid sequence as set forth in SEQ ID NOS: 2, 4 and/or 6.

Some embodiments relate to fragments of SEQ ID NOS: 1, 3, 5, 7, 9, 11 and/or 13. Fragments can comprise at least about 60%, at least about 65%, at least about 70%, at least about 75%, at least about 80%, at least about 85%, at least about 90%, at least about 95%, at least about 96%, at least about 97%, at least about 98%, or at least about 99% of SEQ ID NOS: 1, 3, 5, 7, 9, 11 and/or 13. In some embodiments, fragments can include sequences that encode a leader sequence, for example an immunoglobulin leader sequence, such as an IgE leader sequence. In some embodiments, fragments are free of coding sequences that encode a leader sequence.

Fragments of nucleic acids with nucleotide sequences having identity to fragments of SEQ ID NOS: 1, 3, 5, 7, 9, 11 and/or 13 can be provided. Such fragments can comprise at least 60%, at least 65%, at least 70%, at least 75%, at least 80%, at least 85%, at least 90%, at least 95%, at least 96%, at least 97%, at least 98%, or at least 99% of nucleic acids having 95% or greater identity to SEQ ID NOS: 1, 3, 5, 7, 9, 11 and/or 13. Some embodiments relate to fragments that have 96% or greater identity to the fragments of CD40L nucleic acid sequences herein. Some embodiments relate to fragments that have 97% or greater identity to the fragments of CD40L nucleic acid sequences herein. Some embodiments relate to fragments that have 98% or greater identity to the fragments of CD40L nucleic acid sequences herein. Some embodiments relate to fragments that have 99% or greater identity to the fragments of CD40L nucleic acid sequences herein. In some embodiments, fragments include sequences that encode a leader sequence, for example, an immunoglobulin leader sequence such as the IgE leader sequence. In some embodiments, fragments are free of coding sequences that encode a leader sequence.

Fragments of SEQ ID NOS: 2, 4, 6, 8, 10, 12 and/or 14 can be provided. Fragments can comprise at least 60%, at least 65%, at least 70%, at least 75%, at least 80%, at least 85%, at least 90%, at least 95%, at least 96%, at least 97%, at least 98%, or at least 99% of SEQ ID NOS:2, 4, 6, 8, 10, 12 and/or 14. In some embodiments, fragments include a leader sequence, for example, an immunoglobulin leader sequence such as the IgE leader sequence. In some embodiments, fragments are free of a leader sequence.

Fragments of proteins with amino acid sequences having identity to fragments of SEQ ID NOS:2, 4, 6, 8, 10, 12 and/or 14 can be provided. Such fragments can comprise at least 60%, at least 65%, at least 70%, at least 75%, at least 80%, at least 85%, at least 90%, at least 95%, at least 96%, at least 97%, at least 98%, or at least 99% of proteins having 95% or greater identity to SEQ ID NOS: 2, 4, 6, 8, 10, 12 and/or 14. Some embodiments relate to fragments having 96% or greater identity to the fragments of CD40L protein sequences herein. Some embodiments relate to fragments having 97% or greater identity to the fragments of CD40L protein sequences herein. Some embodiments relate to fragments having 98% or greater identity to the fragments of CD40L protein sequences herein. Some embodiments relate to fragments having 99% or greater identity to the fragments of CD40L protein sequences herein. In some embodiments, fragments include a leader sequence, for example, an immunoglobulin leader sequence such as the IgE leader sequence. In some embodiments, the fragments are free of a leader sequence.

b. Antigen

The vaccine can comprise an antigen or fragment or variant thereof. The antigen can be anything that induces an immune response in a subject. Purified antigens are not usually strong immunogenic on their own and are therefore combined with the adjuvant as described above. The immune response induced by the antigen can be boosted or increased when combined with the adjuvant. Such an immune response can be a humoral immune response and/or a cellular immune response. In some embodiments, the combination of the adjuvant and the antigen can boost or increase a cellular immune response in the subject.

The antigen can be a nucleic acid sequence, an amino acid sequence, or a combination thereof. The nucleic acid sequence can be DNA, RNA, cDNA, a variant thereof, a fragment thereof, or a combination thereof. The nucleic acid sequence can also include additional sequences that encode linker or tag sequences that are linked to the antigen by a peptide bond. The amino acid sequence can be a protein, a peptide, a variant thereof, a fragment thereof, or a combination thereof.

The antigen can be contained in a protein, a nucleic acid, or a fragment thereof, or a variant thereof, or a combination thereof from any number of organisms, for example, a virus, a parasite, a bacterium, a fungus, or a mammal. The antigen can be associated with an autoimmune disease, allergy, or asthma. In other embodiments, the antigen can be associated with cancer, herpes, influenza, hepatitis B, hepatitis C, human papilloma virus (HPV), or human immunodeficiency virus (HIV). Preferably, the antigen can be associated with influenza or HIV.

Some antigens can induce a strong immune response. Other antigens can induce a weak immune response. The antigen can elicit a greater immune response when combined with the adjuvant as described above.

(1) Viral Antigens

The antigen can be a viral antigen, or fragment thereof, or variant thereof. The viral antigen can be from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. The viral antigen can be from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, or cancer causing virus.

(a) Human Papilloma Virus (HPV) Antigen

CD40L can be associated or combined with a human papilloma virus (HPV) antigen, or fragment thereof, or variant thereof. The HPV antigen can be from HPV types 16, 18, 31, 33, 35, 45, 52, and 58 which cause cervical cancer, rectal cancer, and/or other cancers. The HPV antigen can be from HPV types 6 and 11, which cause genital warts, and are known to be causes of head and neck cancer.

The HPV antigens can be the HPV E6 or E7 domains from each HPV type. For example, for HPV type 16 (HPV16), the HPV16 antigen can include the HPV16 E6 antigen, the HPV16 E7 antigen, fragments, variants, or combinations thereof. Similarly, the HPV antigen can be HPV 6 E6 and/or E7, HPV 11 E6 and/or E7, HPV 18 E6 and/or E7, HPV 31 E6 and/or E7, HPV 33 E6 and/or E7, HPV 52 E6 and/or E7, or HPV 58 E6 and/or E7, fragments, variants, or combinations thereof.

(b) RSV Antigen

CD40L can also be associated or combined with an RSV antigen or fragment thereof, or variant thereof. The RSV antigen can be a human RSV fusion protein (also referred to herein as "RSV F", "RSV F protein" and "F protein"), or fragment or variant thereof. The human RSV fusion protein can be conserved between RSV subtypes A and B. The RSV antigen can be a RSV F protein, or fragment or variant thereof, from the RSV Long strain (GenBank AAX23994.1). The RSV antigen can be a RSV F protein from the RSV A2 strain (GenBank AAB59858.1), or a fragment or variant thereof. The RSV antigen can be a monomer, a dimer or trimer of the RSV F protein, or a fragment or variant thereof. The RSV antigen can be an optimized amino acid RSV F amino acid sequence, or fragment or variant thereof.

The postfusion form of RSV F elicits high titer neutralizing antibodies in immunized animals and protects the animals from RSV challenge. The present invention utilizes this immunoresponse in the claimed vaccines. According to the invention, the RSV F protein can be in a prefusion form or a postfusion form.

The RSV antigen can also be human RSV attachment glycoprotein (also referred to herein as "RSV G", "RSV G protein" and "G protein"), or fragment or variant thereof. The human RSV G protein differs between RSV subtypes A and B. The antigen can be RSV G protein, or fragment or variant thereof, from the RSV Long strain (GenBank AAX23993). The RSV antigen can be RSV G protein from: the RSV subtype B isolate H5601, the RSV subtype B isolate H1068, the RSV subtype B isolate H5598, the RSV subtype B isolate H1123, or a fragment or variant thereof. The RSV antigen can be an optimized amino acid RSV G amino acid sequence, or fragment or variant thereof.

In other embodiments, the RSV antigen can be human RSV non-structural protein 1 ("NS1 protein"), or fragment or variant thereof. For example, the RSV antigen can be RSV NS1 protein, or fragment or variant thereof, from the RSV Long strain (GenBank AAX23987.1). The RSV antigen human can also be RSV non-structural protein 2 ("NS2 protein"), or fragment or variant thereof. For example, the RSV antigen can be RSV NS2 protein, or fragment or variant thereof, from the RSV Long strain (GenBank AAX23988.1). The RSV antigen can further be human RSV nucleocapsid ("N") protein, or fragment or variant thereof. For example, the RSV antigen can be RSV N protein, or fragment or variant thereof, from the RSV Long strain (GenBank AAX23989.1). The RSV antigen can be human RSV Phosphoprotein ("P") protein, or fragment or variant thereof. For example, the RSV antigen can be RSV P protein, or fragment or variant thereof, from the RSV Long strain (GenBank AAX23990.1). The RSV antigen also can be human RSV Matrix protein ("M") protein, or fragment or variant thereof. For example, the RSV antigen can be RSV M protein, or fragment or variant thereof, from the RSV Long strain (GenBank AAX23991.1).

In still other embodiments, the RSV antigen can be human RSV small hydrophobic ("SH") protein, or fragment or variant thereof. For example, the RSV antigen can be RSV SH protein, or fragment or variant thereof, from the RSV Long strain (GenBank AAX23992.1). The RSV antigen can also be human RSV Matrix protein 2-1 ("M2-1") protein, or fragment or variant thereof. For example, the RSV antigen can be RSV M2-1 protein, or fragment or variant thereof, from the RSV Long strain (GenBank AAX23995.1). The RSV antigen can further be human RSV Matrix protein 2-2 ("M2-2") protein, or fragment or variant thereof. For example, the RSV antigen can be RSV M2-2 protein, or fragment or variant thereof, from the RSV Long strain (GenBank AAX23997.1). The RSV antigen human can be RSV Polymerase L ("L") protein, or fragment or variant thereof. For example, the RSV antigen can be RSV L protein, or fragment or variant thereof, from the RSV Long strain (GenBank AAX23996.1).

In further embodiments, the RSV antigen can have an optimized amino acid sequence of NS1, NS2, N, P, M, SH, M2-1, M2-2, or L protein. The RSV antigen can be a human RSV protein or recombinant antigen, such as any one of the proteins encoded by the human RSV genome.

In other embodiments, the RSV antigen can be, but is not limited to, the RSV F protein from the RSV Long strain, the RSV G protein from the RSV Long strain, the optimized amino acid RSV G amino acid sequence, the human RSV genome of the RSV Long strain, the optimized amino acid RSV F amino acid sequence, the RSV NS1 protein from the RSV Long strain, the RSV NS2 protein from the RSV Long strain, the RSV N protein from the RSV Long strain, the RSV P protein from the RSV Long strain, the RSV M protein from the RSV Long strain, the RSV SH protein from the RSV Long strain, the RSV M2-1 protein from the RSV Long strain, for the RSV M2-2 protein from the RSV Long strain, the RSV L protein from the RSV Long strain, the RSV G protein from the RSV subtype B isolate H5601, the RSV G protein from the RSV subtype B isolate H1068, for the RSV G protein from the RSV subtype B isolate H5598, the RSV G protein from the RSV subtype B isolate H1123, or fragment thereof, or variant thereof.

(c) Influenza Antigen

CD40L can be associated or combined with an influenza antigen or fragment thereof, or variant thereof. The influenza antigens are those capable of eliciting an immune response in a mammal against one or more influenza serotypes. The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B.

The influenza antigen can also contain at least one antigenic epitope that can be effective against particular influenza immunogens against which an immune response can be induced. The antigen may provide an entire repertoire of immunogenic sites and epitopes present in an intact influenza virus. The antigen may be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen may be a hybrid consensus hemagglutinin antigen sequence that can be derived from combining two different consensus hemagglutinin antigen sequences or portions thereof. Each of two different consensus hemagglutinin antigen sequences may be derived from a different set of a plurality of influenza A virus strains of one serotype such as a plurality of influenza A virus strains of serotype H1. The antigen may be a consensus hemagglutinin antigen sequence that can be derived from hemagglutinin antigen sequences from a plurality of influenza B virus strains.

In some embodiments, the influenza antigen can be H1 HA, H2 HA, H3 HA, H5 HA, or a BHA antigen. Alternatively, the influenza antigen can be a consensus hemagglutinin antigen a protein comprising a consensus H1 amino acid sequence or a consensus H2 amino acid sequence. The consensus hemagglutinin antigen may be a synthetic hybrid consensus H1 sequences comprising portions of two different consensus H1 sequences, which are each derived from a different set of sequences from the other. An example of a consensus HA antigen that is a synthetic hybrid consensus H1 protein is a protein comprising the U2 amino acid sequence. The consensus hemagglutinin antigen may be a consensus hemagglutinin protein derived from hemagglutinin sequences from influenza B strains, such as a protein comprising the consensus BHA amino acid sequence.

The consensus hemagglutinin antigen may further comprise one or more additional amino acid sequence elements. The consensus hemagglutinin antigen may further comprise on its N-terminal an IgE or IgG leader amino acid sequence. The consensus hemagglutinin antigen may further comprise an immunogenic tag which is a unique immunogenic epitope that can be detected by readily available antibodies. An example of such an immunogenic tag is the 9 amino acid influenza HA Tag which may be linked on the consensus hemagglutinin C terminus. In some embodiments, consensus hemagglutinin antigen may further comprise on its N-terminal an IgE or IgG leader amino acid sequence and on its C terminal an HA tag.

The consensus hemagglutinin antigen may be a consensus hemagglutinin protein that consists of consensus influenza amino acid sequences or fragments and variants thereof. The consensus hemagglutinin antigen may be a consensus hemagglutinin protein that comprises non-influenza protein sequences and influenza protein sequences or fragments and variants thereof.

Examples of a consensus H1 protein include those that may consist of the consensus H1 amino acid sequence or those that further comprise additional elements such as an IgE leader sequence, or an HA Tag or both an IgE leader sequence and an HA Tag.

Examples of consensus H2 proteins include those that may consist of the consensus H2 amino acid sequence or those that further comprise an IgE leader sequence, or an HA Tag, or both an IgE leader sequence and an HA Tag.

Examples of hybrid consensus H1 proteins include those that may consist of the consensus U2 amino acid sequence or those that further comprise an IgE leader sequence, or an HA Tag, or both an IgE leader sequence and an HA Tag.

Examples of hybrid consensus influenza B hemagglutinin proteins include those that may consist of the consensus BHA amino acid sequence or it may comprise an IgE leader sequence, or a an HA Tag, or both an IgE leader sequence and an HA Tag.

The consensus hemagglutinin protein can be encoded by a consensus hemagglutinin nucleic acid, a variant thereof or a fragment thereof. Unlike the consensus hemagglutinin protein which may be a consensus sequence derived from a plurality of different hemagglutinin sequences from different strains and variants, the consensus hemagglutinin nucleic acid refers to a nucleic acid sequence that encodes a consensus protein sequence and the coding sequences used may differ from those used to encode the particular amino acid sequences in the plurality of different hemagglutinin sequences from which the consensus hemagglutinin protein sequence is derived. The consensus nucleic acid sequence may be codon optimized and/or RNA optimized. The consensus hemagglutinin nucleic acid sequence may comprise a Kozak's sequence in the 5' untranslated region. The consensus hemagglutinin nucleic acid sequence may comprise nucleic acid sequences that encode a leader sequence. The coding sequence of an N terminal leader sequence is 5' of the hemagglutinin coding sequence. The N-terminal leader can be facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

(d) Human Immunodeficiency Virus (HIV) Antigen

CD40L can be associated or combined with an HIV antigen or fragment thereof, or variant thereof. HIV antigens can include modified consensus sequences for immunogens. Genetic modifications including codon optimization, RNA optimization, and the addition of a high efficient immunoglobulin leader sequence to increase the immunogenicity of constructs can be included in the modified consensus sequences. The novel immunogens can be designed to elicit stronger and broader cellular immune responses than a corresponding codon optimized immunogens.

In some embodiments, the HIV antigen can be a subtype A consensus envelope DNA sequence construct, an IgE leader sequence linked to a consensus sequence for Subtype A envelope protein, or a subtype A consensus Envelope protein sequence.

In other embodiments, the HIV antigen can be a subtype B consensus envelope DNA sequence construct, an IgE leader sequence linked to a consensus sequence for Subtype B envelope protein, or an subtype B consensus Envelope protein sequence In still other embodiments, the HIV antigen can be a subtype C consensus envelope DNA sequence construct, an IgE leader sequence linked to a consensus sequence for subtype C envelope protein, or a subtype C consensus envelope protein sequence.

In further embodiments, the HIV antigen can be a subtype D consensus envelope DNA sequence construct, an IgE leader sequence linked to a consensus sequence for Subtype D envelope protein, or a subtype D consensus envelope protein sequence.

In some embodiments, the HIV antigen can be a subtype B Nef-Rev consensus envelope DNA sequence construct, an IgE leader sequence linked to a consensus sequence for Subtype B Nef-Rev protein, or a Subtype B Nef-Rev consensus protein sequence In other embodiments, the HIV antigen can be a Gag consensus DNA sequence of subtype A, B, C and D DNA sequence construct, an IgE leader sequence linked to a consensus sequence for Gag consensus subtype A, B, C and D protein, or a consensus Gag subtype A, B, C and D protein sequence.

In still other embodiments the HIV antigen can be a MPol DNA sequence or a MPol protein sequence. The HIV antigen can be nucleic acid or amino acid sequences of Env A, Env B, Env C, Env D, B Nef-Rev, Gag, or any combination thereof.

(2) Parasite Antigens

The antigen can be a parasite antigen or fragment or variant thereof. The parasite can be a protozoa, helminth, or ectoparasite. The helminth (i.e., worm) can be a flatworm (e.g., flukes and tapeworms), a thorny-headed worm, or a round worm (e.g., pinworms). The ectoparasite can be lice, fleas, ticks, and mites.

The parasite can be any parasite causing the following diseases: Acanthamoeba keratitis, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

The parasite can be Acanthamoeba, Anisakis, *Ascaris lumbricoides*, Botfly, *Balantidium coli*, Bedbug, *Cestoda* (tapeworm), Chiggers, *Cochliomyia hominivorax, Entamoeba histolytica, Fasciola hepatica, Giardia lamblia*, Hookworm, *Leishmania, Linguatula serrata*, Liver fluke, Loa, *Paragonimus*—lung fluke, Pinworm, *Plasmodium falciparum*, Schistosoma, *Strongyloides stercoralis*, Mite, Tapeworm, *Toxoplasma gondii, Trypanosoma*, Whipworm, or *Wuchereria bancrofti*.

(a) Malaria Antigen

CD40L can be associated or combined with a malaria antigen (i.e., PF antigen or PF immunogen), or fragment thereof, or variant thereof. The antigen can be from a parasite causing malaria. The malaria causing parasite can be *Plasmodium falciparum*. The *Plasmodium falciparum* antigen can include the circumsporozoite (CS) antigen.

In some embodiments, the malaria antigen can be nucleic acid molecules such as plasmids which encode one or more of the *P. falciparum* immunogens CS; LSA1; TRAP; CelTOS; and Ama1. The immunogens may be full length or immunogenic fragments of full length proteins. The immunogens comprise consensus sequences and/or modifications for improved expression.

In other embodiments, the malaria antigen can be a consensus sequence of TRAP, which is also referred to as SSP2, designed from a compilation of all full-length *Plasmodium falciparum* TRAP/SSP2 sequences in the GenBank database (28 sequences total). Consensus TRAP immunogens (i.e., ConTRAP immunogen) may comprise a signal peptide such as an immunoglobulin signal peptide such as an IgE or IgG signal peptide and in some embodiments, may comprise an HA Tag.

In still other embodiments, the malaria antigen can be CelTOS, which is also referred to as Ag2 and is a highly conserved *Plasmodium* antigen. Consensus CelTOS antigens (i.e., ConCelTOS immunogen) may comprise a signal peptide such as an immunoglobulin signal peptide such as an IgE or IgG signal peptide and in some embodiments, may comprise an HA Tag.

In further embodiments, the malaria antigen can be Ama1, which is a highly conserved *Plasmodium* antigen. The malaria antigen can also be a consensus sequence of Ama1 (i.e., ConAmaI immunogen) comprising in some instances, a signal peptide such as an immunoglobulin signal peptide such as an IgE or IgG signal peptide and in some embodiments, may comprise an HA Tag.

In some embodiments, the malaria antigen can be a consensus CS antigen (i.e., Consensus CS immunogen) comprising in some instances, a signal peptide such as an immunoglobulin signal peptide such as an IgE or IgG signal peptide and in some embodiments, may comprise an HA Tag.

In other embodiments, the malaria antigen can be a fusion proteins comprising a combination of two or more of the PF proteins set forth herein. For example, fusion proteins may comprise two or more of Consensus CS immunogen, ConLSA1 immunogen, ConTRAP immunogen, ConCelTOS immunogen and, ConAma1 immunogen linked directly adjacent to each other or linked with a spacer or one more amino acids in between. In some embodiments, the fusion protein comprises two PF immunogens; in some embodiments the fusion protein comprises three PF immunogens, in some embodiments the fusion protein comprises four PF immunogens, and in some embodiments the fusion protein comprises five PF immunogens. Fusion proteins with two Consensus PF immunogens may comprise: CS and LSA1; CS and TRAP; CS and CelTOS; CS and Ama1; LSA1 and TRAP; LSA1 and CelTOS; LSA1 and Ama1; TRAP and CelTOS; TRAP and Ama1; or CelTOS and Ama1. Fusion proteins with three Consensus PF immunogens may comprise: CS, LSA1 and TRAP; CS, LSA1 and CelTOS; CS, LSA1 and Ama1; LSA1, TRAP and CelTOS; LSA1, TRAP and Ama1; or TRAP, CelTOS and Ama1. Fusion proteins with four Consensus PF immunogens may comprise: CS, LSA1, TRAP and CelTOS; CS, LSA1, TRAP and Ama1; CS, LSA1, CelTOS and Ama1; CS, TRAP, CelTOS and Ama1; or LSA1, TRAP, CelTOS and Ama1. Fusion proteins with five Consensus PF immunogens may comprise CS or CS-alt, LSA1, TRAP, CelTOS and Ama1.

In some embodiments, the fusion proteins comprise a signal peptide linked to the N terminus. In some embodiments, the fusion proteins comprise multiple signal peptides linked to the N terminal of each Consensus PF immunogens. In some embodiments, a spacer may be included between PF immunogens of a fusion protein. In some embodiments, the spacer between PF immunogens of a fusion protein may be a proteolyic cleavage site. In some embodiments, the spacer may be a proteolyic cleavage site recognized by a protease found in cells to which the vaccine is intended to be administered and/or taken up. In some embodiments, a spacer may be included between PF immunogens of a fusion protein wherein the spacer is a proteolyic cleavage site recognized by a protease found in cells to which the vaccine is intended to be administered and/or taken up and the fusion proteins comprises multiple signal peptides linked to the N terminal of each Consensus PF immunogens such that upon cleavage the signal peptide of each Consensus PF immunogens translocates the Consensus PF immunogen to outside the cell.

(3) Bacterial Antigens

The antigen can be bacterial antigen or fragment or variant thereof. The bacterium can be from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

The bacterium can be a gram positive bacterium or a gram negative bacterium. The bacterium can be an aerobic bacterium or an anerobic bacterium. The bacterium can be an autotrophic bacterium or a heterotrophic bacterium. The bacterium can be a mesophile, a neutrophile, an extremophile, an acidophile, an alkaliphile, a thermophile, psychrophile, halophile, or an osmophile.

The bacterium can be an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. The bacterium can be a mycobacteria, *Clostridium tetani, Yersinia pestis, Bacillus anthracis*, methicillin-resistant *Staphylococcus aureus* (MRSA), or *Clostridium difficile.*

(4) Fungal Antigens

The antigen can be a fungal antigen or fragment or variant thereof. The fungus can be *Aspergillus* species, *Blastomyces dermatitidis, Candida* yeasts (e.g., *Candida albicans*), *Coccidioides, Cryptococcus neoformans, Cryptococcus gattii*, dermatophyte, *Fusarium* species, *Histoplasma capsulatum*, Mucoromycotina, *Pneumocystis jirovecii, Sporothrix schenckii, Exserohilum*, or *Cladosporium.* c. Vector

The vaccine can comprise one or more vectors that include a nucleic acid encoding the antigen and the adjuvant. The one or more vectors can be capable of expressing the antigen and the adjuvant. The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, or the adjuvant-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Circular and Linear Vectors

The vector may be circular plasmid, which may transform a target cell by integration into the cellular genome or exist extrachromosomally (e.g. autonomous replicating plasmid with an origin of replication).

The vector can be pVAX, pcDNA3.0, or provax, or any other expression vector capable of expressing DNA encoding the antigen, or the adjuvant and enabling a cell to translate the sequence to an antigen that is recognized by the immune system, or the adjuvant.

Also provided herein is a linear nucleic acid vaccine, or linear expression cassette ("LEC"), that is capable of being efficiently delivered to a subject via electroporation and expressing one or more desired antigens, or one or more desired adjuvants. The LEC may be any linear DNA devoid of any phosphate backbone. The DNA may encode one or more antigens, or one or more adjuvants. The LEC may contain a promoter, an intron, a stop codon, and/or a polyadenylation signal. The expression of the antigen, or the adjuvant may be controlled by the promoter. The LEC may not contain any antibiotic resistance genes and/or a phosphate backbone. The LEC may not contain other nucleic acid sequences unrelated to the desired antigen gene expression, or the desired adjuvant expression.

The CD40L vectors can be arranged in a plasmid together or separately as schematically shown in FIG. 1A.

The LEC may be derived from any plasmid capable of being linearized. The plasmid may be capable of expressing the antigen, or the adjuvant. The plasmid may be capable of expressing the adjuvant CD40L, for example, a dual promoter plasmid having the p19 subunit under the control of a first promoter, and the p40 subunit under the control of a second promoter. The first and second promoters may or may not be the same promoters. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen, or encoding the adjuvant, and enabling a cell to translate the sequence to an antigen that is recognized by the immune system, or the adjuvant.

The LEC can be pcrM2. The LEC can be pcrNP. pcrNP and pcrMR can be derived from pNP (Puerto Rico/34) and pM2 (New Caledonia/99), respectively.

(3) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence, or the adjuvant sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination. The promoter may be operably linked to the nucleic acid sequence encoding the adjuvant and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

d. Excipients and Other Components of the Vaccine

The vaccine may further comprise a pharmaceutically acceptable excipient. The pharmaceutically acceptable excipient can be functional molecules such as vehicles, adjuvants other than CD40L, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate is may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to CD40L. The additional adjuvant can be other genes that are expressed in an alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes that can be useful as adjuvants in addition to CD40L include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. Methods of Vaccination

The present invention is also directed to methods of increasing an immune response in a subject by different routes of administration by the vaccine. Increasing the immune response can be used to treat and/or prevent disease in the subject.

The method can include administering the herein disclosed vaccines to the subject. The subject administered the vaccine can have an increased or boosted immune response as compared to a subject administered the antigen alone. In some embodiments, the immune response in the subject administered the vaccine can be increased by at least about 10% to at least about 600%. Alternatively, the immune response in the subject administered the vaccine may be increased by at least about 10% to at least about 250%. In still other alternative embodiments, the immune response in the subject administered the vaccine may be increased by about 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 200%, 205%, 210%, 215%, 220%, 225%, 230%, 235%, 240%, 245%, 250%, 255%, 260%, 265%, 270%, 275%, 280%, 285%, 290%, 295%, 300%, 305%, 310%, 315%, 320%, 325%, 330%, 335%, 340%, 345%, 350%, 355%, 360%, 365%, 370%, 375%, 380%, 385%, 390%, 395%, 400%, 405%, 410%, 415%, 420%, 425%, 430%, 435%, 440%, 445%, 450%, 455%, 460%, 465%, 470%, 475%, 480%, 485%, 490%, 495%, 500%, 505%, 510%, 515%, 520%, 525%, 530%, 535%, 540%, 545%, 550%, 555%, 560%, 565,%, 570%, 575%, 580%, 585%, 590%, 595% or 600%.

In other embodiments, the administered vaccine can increase or boost the immune response in the subject by at least about 1.20-fold, at least about 1.5-fold, at least about 2-fold, at least about 2.5-fold, at least about 3-fold, at least about 4-fold, at least about 5-fold, at least about 6-fold, at least about 7-fold, at least about 8-fold, at least about 9-fold, or at least about 10-fold.

The vaccine dose can be between 1 µg to 10 mg active component/kg body weight/time, and can be 2 µg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. The number of vaccine doses for effective treatment can be 1, 2, 3, 4, 5, 6, 7, 8, 9, or 10.

a. Administration

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a monkey, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Feigner et al. (U.S. Pat. No. 5,580,859, issued Dec. 3, 1996); Feigner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccines can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Feigner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Feigner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241,701; 6,233,482; 6,216,034; 6,208,893; 6,192,270; 6,181,964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520,950; 7,171,264; 6,208,893; 6,009,347; 6,120,493; 7,245,963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Plymouth Meeting Pa.) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The CELLECTRA® device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during electroporation. This is particularly advantageous as it means that the electric field is applied to the same area as the injected fluid. There has traditionally been a problem with electroporation in that it is very difficult to accurately align an electrode with previously injected fluid and so user's have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

The present invention has multiple aspects, illustrated by the following non-limiting examples.

3. Examples

Synthetic genes were constructed, each encoding for a different form of CD40L, and cloned into the plasmid backbone pGX0001. A WT CD40L (WT or wild type) variant was a codon and RNA-optimized version of the native CD40 ligand gene in which both the membrane bound and solubilized form of CD40L was expressed. A MT CD40L (MT or mature/soluble) variant was a codon and RNA-optimized alteration of the CD40L sequence in which the membrane-spanning region of the gene was removed to allow the cell to directly release the protein without first inserting it into the cell membrane. A UC CD40Lm (UC or uncleavable) variant was a codon and RNA-optimized alteration of the CD40L sequence in which a mutation was been made within the cleavage domain of the CD40L sequence so the protein was no longer able to be cleaved from the cell membrane and remained attached to the cell in which it was expressed. Each insert also included an efficient IgE leader sequence. The insert were then cloned into the pVAX vector where expression was controlled under a CMV (cytomegalovirus) promoter (FIG. 1A).

All plasmids expressed in vitro as determined by transfection of HEK 293T cells and Western blot of cell lysate (FIG. 1B).

Example 1

Intramuscular Immunization

Mice (C57BL/6 mice, n=5 per group) were used as a model system to determine whether CD40L could function as an adjuvant when the vaccine was administered via an intramuscular route. The vaccine included a human immunodeficiency virus (HIV) envelope consensus clade c protein antigen and CD40L, both of which were encoded by respective plasmids.

Five groups of mice were utilized. A first group of mice were immunized with a pVax backbone (naïve). A second group of mice were immunized with 2.5 μg of HIV envelope consensus clade c (HIV antigen). A third group of mice were immunized with the HIV antigen in combination with 15 μg UC CD40L. A fourth group of mice were immunized with the HIV antigen in combination with 15 μg MT CD40L. A fifth group of mice were immunized with the HIV antigen in combination with 15 μg WT CD40L.

All mice were immunized by the intramuscular route using electroporation (CELLECTRA® electroporation device, Inovio Pharmaceuticals, Plymouth Meeting Pa.). The mice were immunized 3 times (weeks 0, 3, and 6) and sacrificed one week following the final immunization (week 7) (FIG. 2A) and splenocytes collected for cellular analysis as well as blood collected to determine antibody titers induced. Intracellular cytokine staining was performed to measure IFN-γ, IL-2, and TNF-α cytokine production from antigen specific CD4+ and CD8+ T cells following immunization.

As shown in FIG. 2C, the presence of CD40L, in any form, did not significantly alter IFN-γ, IL-2, and TNF-α production from CD4+ T cells generated in response to immunization with HIV envelope consensus clade c. Response frequencies approached 1% for all other groups in each measurement of cytokine production, however, the percent of antigen specific T cells producing cytokine was enhanced by the inclusion of some forms of CD40L (FIG. 2C). IFN-γ was elevated in CD8+ T cells after vaccination with HIV antigen+UC CD40L (approximately 5.0%), HIV antigen+MT CD40L (approximately 9.0%), and HIV antigen+WT CD40L (approximately 8.0%) compared to HIV antigen alone (approximately 6.5%). Mice immunized with HIV antigen+MT had significantly higher IFN-γ production compared to those immunized with HIV antigen alone (p<0.05) and those immunized with HIV antigen+UC (p<0.001). Mice immunized with the WT CD40L had significant increases in antigen specific IFN-γ production compared to the group that received the UC CD40L (p<0.05). For IL-2 in CD8+ T-cells, responses were approximately 1% for all immunized groups. However, the group immunized with HIV antigen+MT had significantly higher IL-2 production compared to the HIV antigen alone (p<0.01) and the HIV antigen+UC p<0.05) groups. TNF-α production from CD8+ T-cells of mice immunized with HIV antigen alone showed a frequency of approximately 3% while HIV antigen+MT, HIV antigen+UC, and HIV antigen+WT showed increases to 5.0%, 3.0% and 5.0% respectively. Mice immunized with HIV antigen+MT or HIV antigen+WT each had significantly increased TNF-α production compared to those immunized with HIV alone (p<0.01 and p<0.05, respectively). These HIV antigen+MT or HIV antigen+WT groups also had significantly higher responses compared to the HIV antigen+UC group (p<0.01 and p<0.05, respectively) (FIG. 2C). Immunization with HIV antigen alone and HIV plus all 3 forms of CD40L (MT, UC or WT) elicited high-titer antibody responses compared to naïve alone (FIG. 2B). Mice immunized with HIV antigen+MT or HIV antigen+ WT each had significantly higher antibody responses compared to HIV alone (p<0.05) and HIV+UC (p<0.05). Overall the MT form of CD40L increased antibody titers compared to the other forms of CD40L (UC or WT).

Example 2

Intramuscular Immunization

Mice (C57BL/6 mice, n=5 per group) were used as a model system to determine whether CD40L could function as an adjuvant when the vaccine was administered via an intramuscular route. The vaccine included an Human Papilloma Virus E6/E7 proteins and CD40L, which were encoded by respective plasmids.

Five groups of mice were utilized. A first group of mice were immunized with a pVax backbone (naïve). A second group of mice were immunized with 10 μg of a plasmid encoding the HPV Type 16 E6/E7 proteins (HPV antigen). A third group of mice were immunized with the HPV antigen in combination with 15 μg UC CD40L. A fourth group of mice were immunized with the HPV antigen in combination with 15 μg MT CD40L. A fifth group of mice were immunized with the HPV antigen in combination with 15 μg WT CD40L.

All mice were immunized by the intramuscular route using electroporation (CELLECTRA® electroporation device, Inovio Pharmaceuticals). Mice were immunized twice with either HPV E6/E7 DNA alone or in combination with one of the CD40L isoforms (weeks 0 and 3) and sacrificed one week following final immunization (week 4). One week after final vaccination, IFN-γ production was determined by ELISpot. In addition, splenocytes isolated from vaccinated mice were stimulated with E7/E6 peptides followed by intracellular staining to measure IFN-γ, TNF-α, and IL-2 cytokine production from antigen-specific CD4+ and CD8+ T cells following immunization (FIG. 4C). Mice were implanted with 5×10⁴ TC 1 cells on day 0. On days 4, 11, 18 and 25 (FIG. 4D), mice were vaccinated with either HPV only or in combination with soluble CD40L. Tumor measurements were taken every week following implantation. It was determined there was increased efficacy of therapeutic vaccination upon tumor challenge with TC1 cells (FIG. 4E).

Example 3

Intramuscular Immunization

Mice (C57BL/6 mice, n=5 per group) were used as a model system to determine whether CD40L could function as an adjuvant when the vaccine was administered via an intramuscular route. The vaccine included a consensus influenza H1HA (Flu) antigen) and CD40L, both of which were encoded by respective plasmids.

Five groups of mice were utilized. A first group of mice were immunized with a pVax backbone (naïve). A second group of mice were immunized with 1 μg of a plasmid encoding the consensus influenza H1HA flu antigen (Flu antigen). A third group of mice were immunized with the Flu antigen in combination with 15 μg UC CD40L. A fourth group of mice were immunized with the Flu antigen in combination with 15 μg MT CD40L. A fifth group of mice were immunized with the Flu antigen in combination with 15 μg WT CD40L.

Figures 5, 5C:
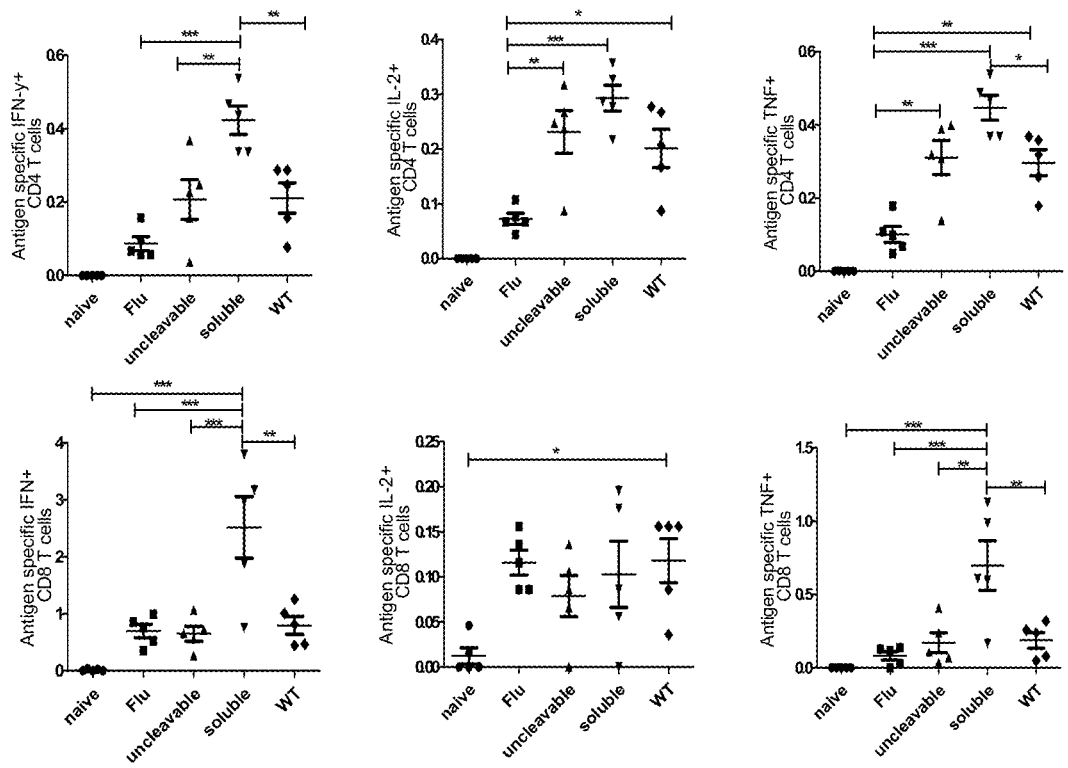
FIG. 5 shows (A) an immunization schedule (immunized twice) with either the consensus influenza H1HA antigen alone or in combination with one of the CD40L isoforms; (B) endpoint binding titers to H1HA (New Caledonia) one week after final vaccination; (C) a measurement of IFN-γ, IL-2, and TNF-α cytokine production from antigen specific CD4+ and CD8+ T cells following immunization, specifically, splenocytes isolated from vaccinated mice stimulated with H1HA consensus peptides following by intracellular staining.

All mice were immunized by the intramuscular route using electroporation (CELLECTRA® electroporation device, Inovio Pharmaceuticals). Mice were immunized twice (weeks 0 and 3) and sacrificed one week following final immunization (week 4) (FIG. 5A). Intracellular cytokine staining was performed to measure IFN-γ, TNF-α, and IL-2 cytokine production from antigen-specific CD4+ and CD8+ T cells following immunization (FIG. 5C).

Responses, as gauged by intracellular cytokine staining, reveal that IFN-γ was elevated in both CD4+ and CD8+ T cells of vaccinated mice compared to the naïve group (0.0%). FIG. 5C shows that IFN-γ produced from CD4+ T cells was significantly increased following immunization with Flu antigen+MT (approximately 0.4%,) compared to Flu alone (approximately 0.08%, p<0.001). Furthermore, CD4+ T cells producing IFN-γ in Flu antigen+MT immunized mice were significantly elevated compared to Flu antigen+UC (0.2%, p<0.01) and to Flu antigen+WT (0.2%, p<0.01). CD8+ T cells producing IFN-γ from Flu antigen+ MT immunized mice (roughly 0.25%) were significantly increased compared to Flu antigen alone, Flu antigen+UC and Flu antigen+WT (all approximately 0.08%, p<0.001, p<0.001, and p<0.01, respectively) (FIG. 5C). For IL-2 in CD4+ T cells Flu antigen alone (approximately 0.07%) was significantly lower than Flu antigen+UC (approx. 0.23%, p<0.01), Flu antigen+MT (approximately 0.28%, p<0.001) and Flu antigen+WT (approximately 0.20%, p<0.05) (FIG. 5C). In CD8+ T cells, levels of IL-2 production were low, with only Flu antigen+WT (0.12%) being significantly greater than naïve (0.01%, p<0.05) (FIG. 5C). For all other groups (Flu antigen alone, UC and MT) there were no significant differences. Lastly, TNF-α produced from CD4+ T cells of Flu antigen+MT immunized mice (approximately 0.45%) were significantly higher than immunization with Flu alone (approximately 0.1%, p<0.001) and Flu antigen+ WT (approximately 0.3%, p<0.05). Both Flu antigen+WT and Flu antigen+UC immunization groups had significantly higher levels of TNF-α in CD4+ T cells compared to Flu antigen alone (both p<0.01). For CD8+ T cells, TNF-α was significantly elevated after immunization with Flu antigen+MT (approximately 0.7%) compared to all other groups (naïve p<0.001, Flu antigen alone p<0.001, Flu antigen+UC p<0.01 and Flu antigen+WT p<0.01).

Immunization with Flu antigen vaccine and Flu antigen vaccine plus all 3 forms of CD40L elicited high-titer antibody responses compared to naïve alone. There were no significant differences between any of the groups; however, the WT form of CD40L had a trend toward increased antibody levels compared to the other forms of CD40L.

The above data from the intramuscular immunizations showed that CD40L has the surprising ability to function as an adjuvant when administered by intramuscular routes. CD40L augmented the cellular immune response in muscle tissues irrespective of the identity or source of the antigen. Each of the plasmids, when co-delivered with one or more plasmid-encoded vaccine antigens using constant-current in vivo electroporation, increased antigen specific cellular immune responses to the encoded antigen(s) (as measured by Interferon Gamma ELISpot assays), as well as antigen specific humoral immune responses to the encoded antigen(s) (as measured by an ELISA looking at the IgG antibody isotype as compared to responses generated by delivering antigen alone).

Example 4

Mice (C57BL/6 mice, n=5 per group) were immunized two times (weeks 0 and 3) with either HIV consensus clade c gp120 alone or in combination with CD40L isoforms followed by an 8 week rest before sacrificing. FIGS. 3A, 3B (endpoint binding titers to consensus clade c gp120 (determined during memory phase)) and 3C (splenocytes isolated from vaccinated mice stimulated following by intracellular staining) show that some variant forms of CD40L maintain or enhance vaccine induced responses in the memory phase.

Example 5

Intramuscular Immunization

Mice (C57BL/6 mice, n=5 per group) were used as a model system to determine whether CD40L could function as an adjuvant when the vaccine was administered via an intramuscular route. The vaccine included a human papilloma virus Type 16 (HPV) vaccine expressing the oncogenic proteins E6 and E7; and CD40L, both of which were encoded by respective plasmids as shown in FIGS. 6A and 6B. All mice were immunized by the intramuscular route using electroporation (CELLECTRA® electroporation device, Inovio Pharmaceuticals, Plymouth Meeting Pa.).

Five groups of mice were utilized. A first group of mice were immunized with a pVax backbone (naïve). A second group of mice were immunized with 10 μg of HPV (HPV antigen). A third group of mice were immunized with the HPV antigen in combination with 15 μg UC CD40L. A fourth group of mice were immunized with the HPV antigen in combination with 15 μg MT CD40L. A fifth group of mice were immunized with the HPV antigen in combination with 15 μg WT CD40L.

Figures 7, 7C:
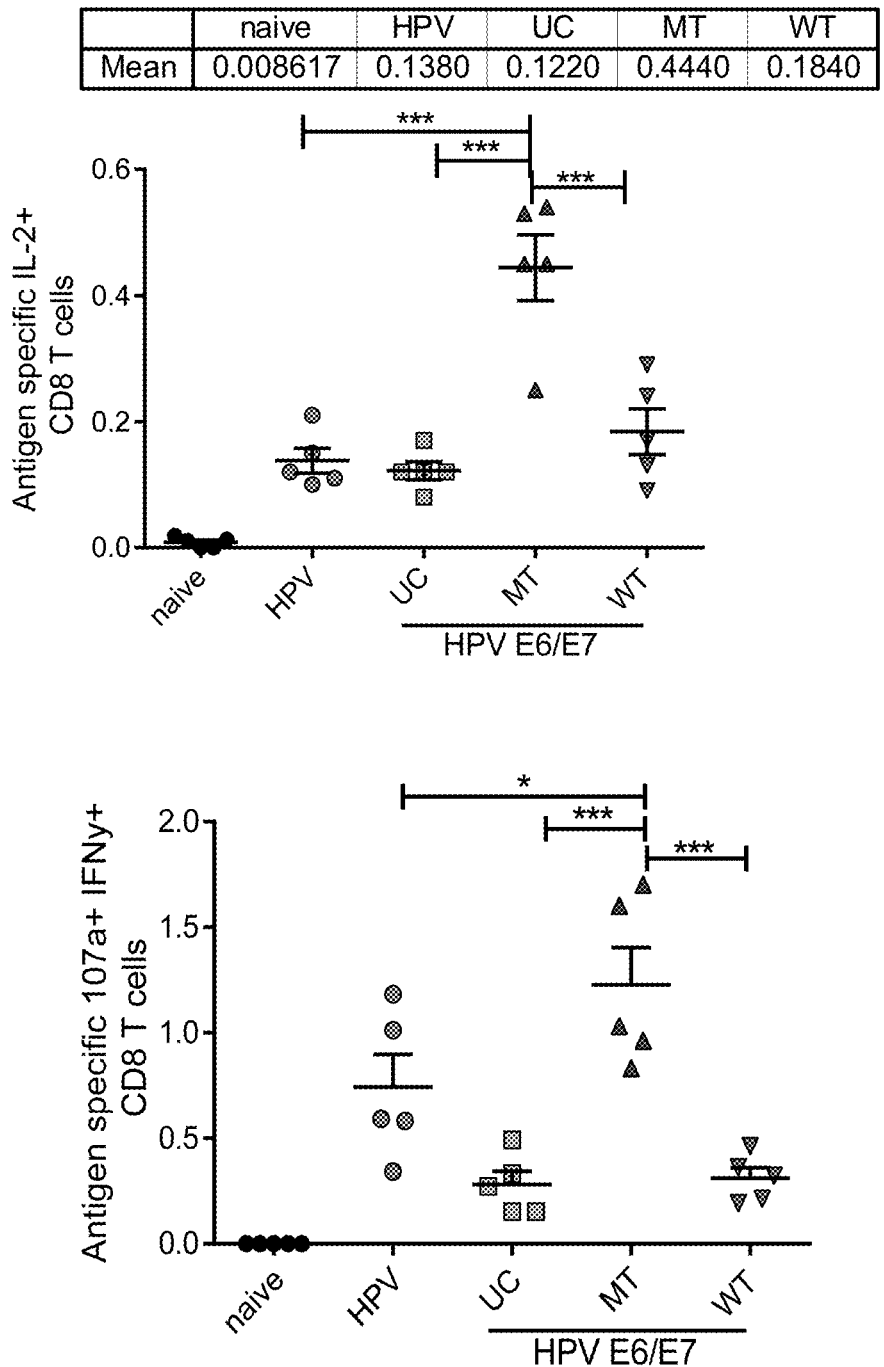
FIG. 7 shows mature CD40L increase CD8 T cell responses: (A) mice were immunized two times with either HPV16 E6/E7 DNA alone or in combination with CD40L isoforms; (B) one week after final vaccination, IFN-γ production was determined by ELISpot; (C) splenocytes isolated from vaccinated mice were stimulated with E7/E6 peptides followed by intracellular staining; (D) polyfunctionality of CD8 T cell responses were assessed.

The mice were immunized 2 times at three week intervals (weeks 0 and 3) and sacrificed one week following the final immunization (week 4) (FIG. 7A) and splenocytes collected and isolated and stimulated with E6/E7 peptides following intracellular staining for cellular analysis as well as blood collected to determine antibody titers induced. As shown in FIG. 7B, one week after final vaccination, IFN-γ production, as determined by ELISpot, increased with respect to the mice immunized with HPV antigen+MT. Intracellular cytokine staining was performed to measure IFN-γ, IL-2, and TNF-α cytokine production from antigen specific CD4+ and CD8+ T cells following immunization (FIG. 7C). Polyfunctionality of CD8+ T cell responses was also assessed along with pie charts showing the percent of cells expressing 4, 3, 2, or 1 function (significance determined by modified ANOVA *<0.05, <0.01, *<0.001) (FIG. 7D). IFN-γ was elevated in CD8+ T cells after vaccination with HPV antigen+MT CD40L compared to HPV antigen alone. Mice immunized with HPV antigen+MT had significantly higher IFN-γ production compared to those immunized with HPV antigen alone. For IL-2 in CD8+ T cells the group immunized with HPV antigen+MT had significantly higher IL-2 production compared to the HPV antigen alone. TNF-α production from CD8+ T-cells of mice immunized with HPV antigen alone showed a frequency of less than 1% while HPV antigen+MT, showed increases to over 2%. Mice immunized with HPV antigen+MT had significantly increased TNF-α production compared to those immunized with HPV alone.

Figures 8, 8B:
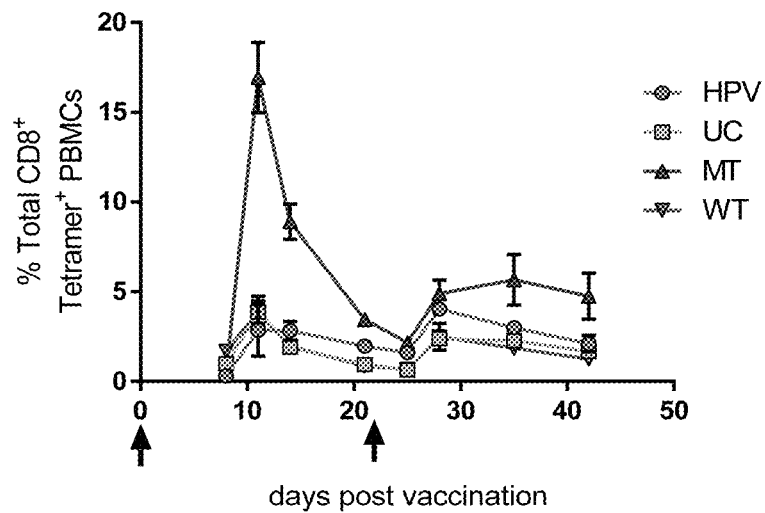
FIG. 8 shows tetramer specific responses against the E7 epitope (H-2Db HPV16 E7 (RAHYNIVTF)) increase with inclusion of mature CD40L: (A) mice were immunized two times with either HPV16 E6/E7 DNA alone or in combination with CD40L isoforms. One week after final vaccination, tetramer specific responses were determined in the spleen and in PBMCs; (B) tetramer specific responses in the periphery were assessed over time. Mice were immunized two times at three week intervals and serially bled. (C) To determine the role of CD4 T cells at day 11 peak tetramer responses, mice were given either CD4 depleting antibody or isotype control and then vaccinated. Tetramer specific responses in the blood were assessed over time (both 11 and 28 days); (D) Lymphocytes were stained with HPV E7 (H-2Db RAHYNIVTF) tetramer which is the dominant epitope in the E7 protein. Representative flow plots of CD8+ cells which are tetramer+. Cells were gated on singles, lymphocytes, CD8+ live cells.

One week after final vaccination (week 4) tetramer specific responses were determined in the spleen and in peripheral blood mononuclear cells (PBMCs). Results show tetramer specific responses against the E7 epitope (H-2D$^b$ HPV16 E7 (RAHYNIVTF)) in the spleen and PBMCs increase with inclusion of MT CD40L (FIG. 8A). In addition, tetramer specific responses in the periphery were assessed over time, where the mice were immunized two times at three week intervals (days 0 and 21) and serially bled to isolate and stain PBMCs (significance determined by modified ANOVA *<0.05, <0.01 *<0.001) (FIG. 8B). To determine the role of CD4 T cells at day 11 peak tetramer responses, mice were given either CD4 depleting antibody or isotype control and then vaccinated. Tetramer specific responses in the blood were assessed over time (FIG. 8C).

Figures 9, 9A:
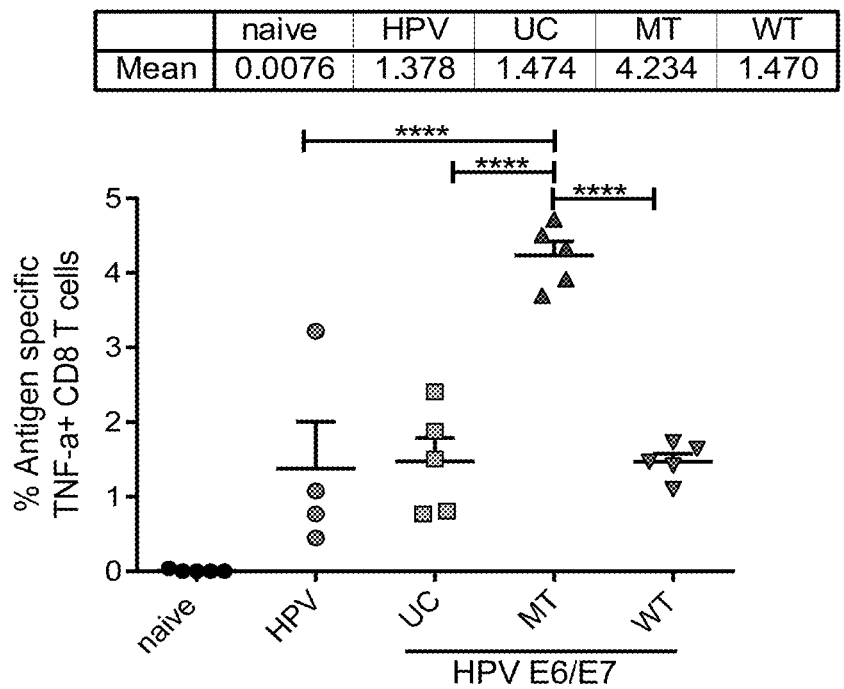
FIG. 9 shows CD8 T cell responses at day 11 (peak tetramer response) express numerous cytokines and degranulation markers: (A) mice were immunized with either HPV16 E6/E7 DNA alone or in combination with CD40L isoforms. Eleven days later, mice were sacrificed and T cell responses were assessed by intracellular cytokine staining. (B) Expression of IFN-γ, 107a and Tbet in antigen specific CD8 T cells. (C) Tetramer specific response in both the PBMCs and splenocytes. (D) Polyfunctionality of CD8+ T cell responses as well as percent of polyfunctionality.
Figures 9, 9C:
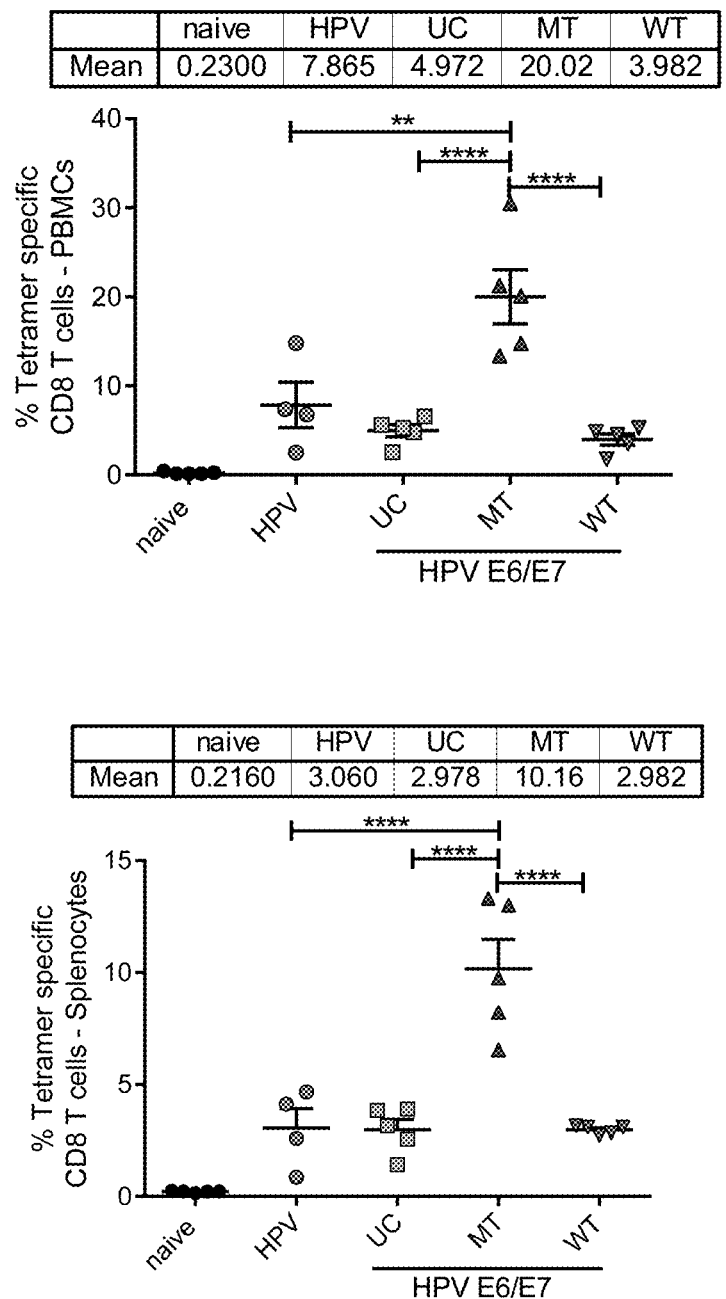

Mice (C57BL/6 mice, n=5 per group) were vaccinated and 11 days after vaccination the mice were sacrificed and immune responses assessed. CD8+ T cell responses at day 11 (peak tetramer response) after first vaccination show expression of numerous cytokines and degranulation markers. Mice immunized with HPV antigen+MT had significantly higher IFN-γ, 107a and Tbet production in antigen specific CD8 T cells compared to those immunized with HPV antigen alone (p<0.05), as shown in FIGS. 9A and 9B. FIG. 9C shows a significant increase in tetramer specific response in both the PBMCs and splenocytes.

Figures 10, 10A:
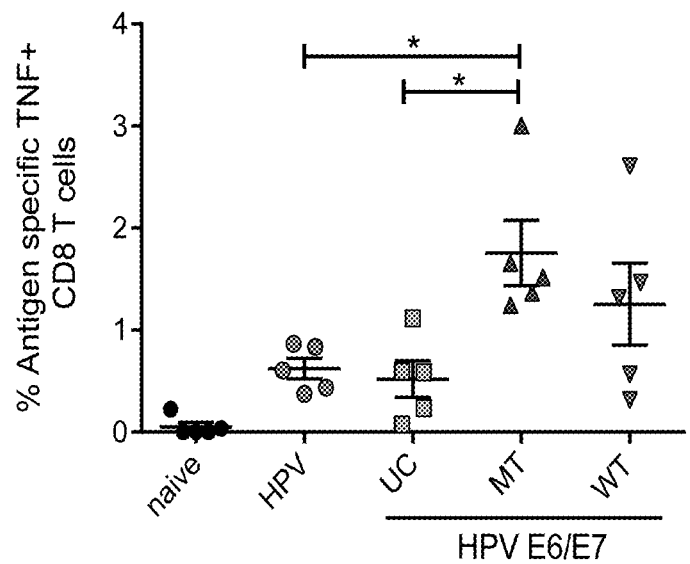
FIG. 10 shows CD8 T cell responses were maintained into memory: mice were immunized two times with either HPV E6/E7 DNA alone or in combination with CD40L isoforms. Eight weeks after final vaccination, CD8 T cell responses were determined by (A) ICS and (B) tetramer staining.

FIGS. 10A and 10B show CD8 responses were maintained into memory. Mice were immunized two times with either HPV E6/E7 DNA alone or in combination with CD40L isoforms. Eight weeks after final vaccination (week 11), CD8 T cell responses were determined by ICS and tetramer staining.

Figures 12, 12C:
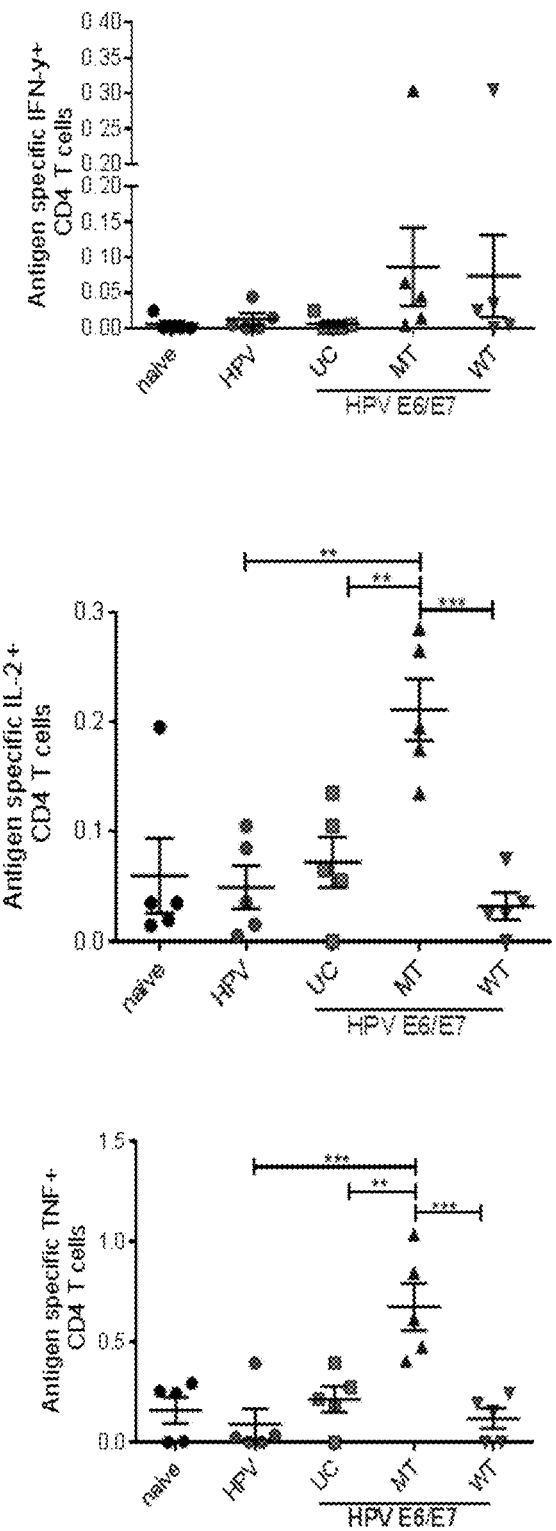
FIG. 12 shows humoral and CD4 responses observed in the mice set forth in FIG. 7.

Humoral and CD4 responses were also assessed as well as shown in FIGS. 12A, 12B and 12C.

Example 6

Tumor Clearance

Figures 11, 11C:
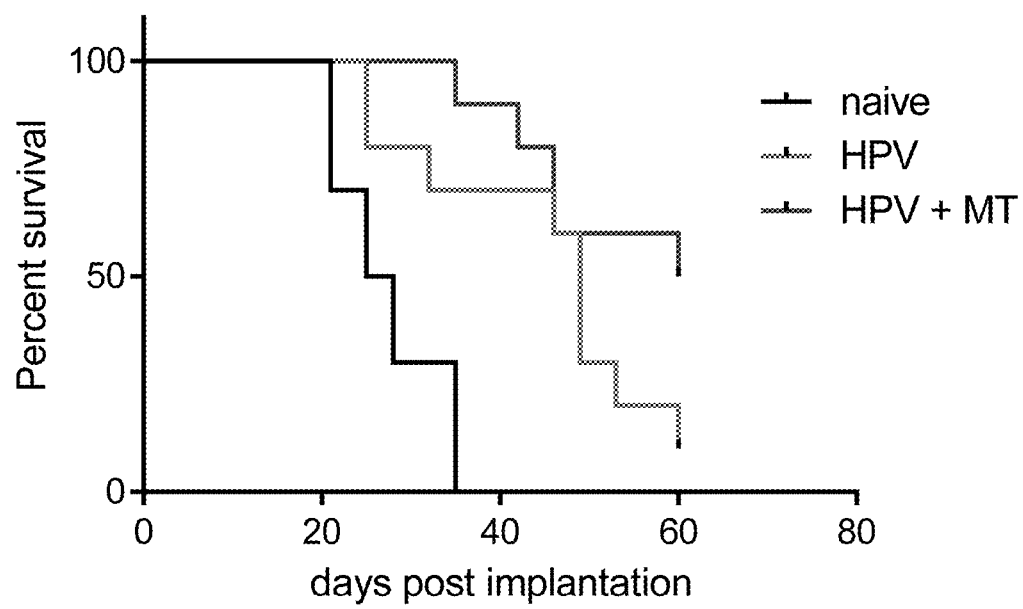
FIG. 11 shows HPV+MT CD40L significantly increases tumor clearance above HPV alone. (A) Mice (n=10) were implanted with 5×10⁴ TC1 cells. One week later mice were immunized with one of the following: pVAX backbone (naïve), HPV alone, or HPV+the various CD40L constructs. Tumor growth was monitored twice a week. (B) Tumor volume of individual mice over time. (C) Survival curves of naïve, HPV alone and HPV+MT CD40L.

Mice (C57BL/6 mice, n=10) were implanted with 5×10$^4$ TC1 cells. One week later mice were immunized with one of the following: pVAX backbone (naïve), HPV alone, or HPV+the various CD40L constructs followed by a boost at days 14, 21 and 28 (FIG. 11A). All mice were immunized by the intramuscular route using electroporation (CELLEC-TRA® electroporation device, Inovio Pharmaceuticals, Plymouth Meeting Pa.). Tumor growth was monitored twice a week. FIG. 11B shows tumor volume of individual mice over time. FIG. 11C shows the survival curves of naïve, HPV alone and HPV+MT CD40L. The results show a significant difference in tumor growth and HPV+MT CD40L significantly increases tumor clearance in comparison to HPV alone (HPV p<0.0001), UC CD40L (p<0.0001) and WT CD40L (p<0.05)). When used as a therapeutic vaccination, mature CD40L increase vaccine efficacy in a TC1 challenge model compared to HPV vaccination alone.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A immunogenic composition comprising:
   a) at least one selected from the group consisting of an antigen and a first nucleic acid sequence encoding the antigen; and
   b) a second nucleic acid sequence encoding a CD40L, or a nucleic acid sequence encoding an immunogenic fragment of the CD40L,
      wherein the second nucleic acid sequence encoding the CD40L comprises at least 90% identity to the nucleic acid sequence of SEQ ID NOs: 1, 3, 5, 7, 9 or 11, and
      wherein the fragment comprises at least 90% identity to the nucleic acid sequence of SEQ ID NOs: 1, 3, 5, 7, 9 or 11; and
   wherein the antigen is encoded by the first nucleic acid sequence and the CD40L is encoded by the second nucleic acid sequence.

2. The immunogenic composition of claim 1, wherein the second nucleic acid sequence comprises any one of SEQ ID NOs: 1, 3, 5, 7, 9 or 11.

3. The immunogenic composition of claim 1, wherein the first nucleic acid sequence encodes an immunogenic fragment of the antigen and the second nucleic acid sequence encodes an immunogenic fragment of the CD40L.

4. The immunogenic composition of claim 1, wherein the antigen is selected from the group consisting of a human papilloma virus (HPV) antigen, a human immunodeficiency virus (HIV) antigen, an influenza antigen, and a *Plasmodium falciparum* antigen.

5. The immunogenic composition of claim 4, wherein the HIV antigen is selected from the group consisting of Env A, Env B, Env C, Env D, B Nef-Rev, Gag, and combinations thereof.

6. The immunogenic composition of claim 4, wherein the influenza virus antigen is selected from the group consisting of H1 HA, H2 HA, H3 HA, H5 HA, BHA antigen, and combinations thereof.

7. The immunogenic composition of claim 4, wherein the *Plasmodium falciparum* antigen comprises a circumsporozoite (CS) antigen.

8. The immunogenic composition of claim 4, wherein the HPV antigen is selected from the group consisting of E6 antigen, E7 antigen, and combinations thereof.

9. The immunogenic composition of claim 1, further comprising a pharmaceutically acceptable excipient.

10. The immunogenic composition of claim 1, wherein the first nucleic acid sequence and second nucleic acid sequence are in the form of an expression vector.

11. The immunogenic composition of claim 10, wherein the first nucleic acid sequence and the second nucleic acid sequence are present in the same expression vector.

12. The immunogenic composition of claim 10, wherein the first nucleic acid sequence and the second nucleic acid sequence are present in different expression vectors.

13. The immunogenic composition of claim 10, wherein the expression vector is a plasmid.

14. A method for inducing an immune response in a subject in need thereof, the method comprising administering the immunogenic composition of claim 1 to the subject, whereby the first nucleic acid sequence and second nucleic acid sequence are expressed in the subject and an immune response is induced in the subject.

15. The method of claim 14, wherein administering the immunogenic composition comprises intramuscular administration or intradermal administration.

16. The method of claim 14, wherein administering the immunogenic composition includes electroporation.

17. The method of claim 14, wherein the immune response is induced in a skin tissue and/or a muscle tissue of the subject.

18. The method of claim 14, wherein the immune response comprises a cellular immune response, a humoral immune response, or both cellular and humoral immune responses in a subject.

* * * * *